(12) United States Patent
Martin

(10) Patent No.: US 10,813,893 B2
(45) Date of Patent: Oct. 27, 2020

(54) COMPOSITIONS AND METHODS FOR THE TREATMENT AND PREVENTION OF CHRONIC HYPOXEMIA AND DYSPNEA

(71) Applicant: Alain Martin, Flemington, NJ (US)

(72) Inventor: Alain Martin, Flemington, NJ (US)

(73) Assignee: CELLULAR SCIENCES, INC., Flemington, NJ (US)

( * ) Notice: Subject to any disclaimer, the term of this patent is extended or adjusted under 35 U.S.C. 154(b) by 0 days.

(21) Appl. No.: 15/441,552

(22) Filed: Feb. 24, 2017

(65) Prior Publication Data

US 2018/0243246 A1 Aug. 30, 2018

(51) Int. Cl.

| | | |
|---|---|---|
| *A61K 31/19* | (2006.01) |
| *A61K 33/06* | (2006.01) |
| *A61K 33/42* | (2006.01) |
| *A61K 45/06* | (2006.01) |
| *A61K 31/56* | (2006.01) |
| *A61K 31/58* | (2006.01) |
| *A61K 31/573* | (2006.01) |
| *A61K 31/198* | (2006.01) |
| *A61K 31/455* | (2006.01) |
| *A61K 31/4174* | (2006.01) |

(52) U.S. Cl.
CPC ............ *A61K 31/19* (2013.01); *A61K 31/198* (2013.01); *A61K 31/4174* (2013.01); *A61K 31/455* (2013.01); *A61K 31/56* (2013.01); *A61K 31/573* (2013.01); *A61K 31/58* (2013.01); *A61K 33/06* (2013.01); *A61K 33/42* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2002/0006961 A1* | 1/2002 | Katz | A61K 9/0043 514/625 |
| 2009/0181007 A1* | 7/2009 | Gennero | A61L 27/3895 424/94.64 |
| 2010/0070417 A1* | 3/2010 | Flynn | H04W 12/06 705/51 |

\* cited by examiner

*Primary Examiner* — Abigail Vanhorn

(57) ABSTRACT

The present invention has shown that not all salts of pyruvic acid enhance lung functions or enhance the synthesis of lung surfactants and that certain salts of pyruvic acid with the correct concentrations of calcium, phosphate and magnesium, are synergistic in their ability to enhance the synthesis of lung surfactants that will enhance lung alveoli functions, while decreasing coughing and lung tightness, and increasing oxygen saturation values to prevent hypoxemia. This patent demonstrates that the sodium pyruvate formula with calcium, phosphate and magnesium was superior over standard sodium pyruvate formula in saline alone in the removal of mucus, reduction of lung or sinus infections, and in reducing drug side effects and congestion. The use of this formula clearly demonstrated that it can be used to produce better efficacy in patients with hypoxemia, with lung and sinus diseases including, asthma, COPD, cystic fibrosis, interstitial lung disease, allergic rhinitis, sinusitis, Alzheimer's, disease, Parkinson's disease, brain trauma, nicotine addiction, sleep apnea, autism, migraine headaches, sleep disorders, lung and sinus infections, cancer therapy with cancer drugs, nicotine addiction, and medications that cause a decrease in lung surfactants.

6 Claims, No Drawings

COMPOSITIONS AND METHODS FOR THE TREATMENT AND PREVENTION OF CHRONIC HYPOXEMIA AND DYSPNEA

FIELD OF THE INVENTION

The present invention relates generally to compositions that enhance the synthesis of lung surfactants, decreased by lung diseases or injuries. The present invention is based on the discovery that the pulmonary dysfunction, characteristic of certain disease states, is attributable to the decrease in the synthesis of a number of surfactant and other secretory molecules normally produced by type H alveolar cells, leading to lung tightness, reduced lung capacity and volume, coughing, dyspnea and Hypoxemia

BACKGROUND OF THE INVENTION

The present invention is based on the discovery that the pulmonary dysfunction, characteristic of certain disease states is attributable to the decrease in the synthesis of surfactants and other secretory molecules normally produced by type II alveolar cells. This decrease in synthesis is believed to be caused by the low levels of key lung nutrients that results in abnormally functioning mitochondria in alveoli leading to lung tightness, reduced lung capacity and volume, coughing, dyspnea and Hypoxemia. It is believed that nutrient depleted or injured or damaged alveoli's cause a generalized decrease in the normal rate of membrane trafficking within the type II cells results in a generalized defect in the synthesis and secretory process, including secondary effects which involve a significant decrease in the level of the synthesis of membrane phospholipids. Type II (Great Alveolar) cells that secrete pulmonary surfactants needed to lower the surface tension of water and allows the membrane to separate, therefore increasing its capability to exchange gases that maintain SaO2 oxygen saturation at or near 100%. Surfactant is continuously released by exocytosis. It forms an underlying aqueous protein-containing hypophase and an overlying phospholipid film composed primarily of dipalmitoyl phosphatidylcholine.

This decrease in the synthesis of surfactants in turn causes an increase in surface tension of the aqueous film bathing the luminal aspect of the alveolar space, a decrease in the elastic properties of pulmonary tissue, a concomitant decrease in the rate of gas exchange within the alveolus, and an overall decrease in pulmonary function causing lung tightness, breathlessness, increased coughing, and a decrease in lung capacity. As a result, the patient develops a pulmonary disease syndrome, including hampered breathing and inefficient gas exchange, with low $SaO_2$ levels called chronic hypoxemia. Reinflation of the alveoli following exhalation is made easier by pulmonary surfactant, which is a phospholipid and protein mixture that reduces surface tension in the thin fluid coating within all alveoli. Insufficient pulmonary surfactant in the alveoli can contribute to atelectasis (collapse of part or all of the lung). Without pulmonary surfactant, atelectasis is a certainty; however, there are other causes of lung collapse such as trauma (pneumothorax), COPD, and pleuritis.

Decrease in lung surfactants also cause coughing and breathlessness. Cough is usually the first symptom to develop along with sputum (phlegm). It tends to come and go at first, and then gradually becomes more persistent (chronic). You may think of your cough as a 'smokers cough' in the early stages of the disease. It is when the breathlessness begins that people often become concerned. Breathlessness ('shortness of breath') and wheezing may occur only when you exert yourself at first, for example, when you climb stairs. These symptoms tend to become gradually worse over the years if you continue to smoke. Difficulty with breathing may eventually become quite distressing. The damaged airways generally make a lot more mucus than normal. This forms sputum (phlegm). You tend to cough up a lot of sputum each day. Chest infections are more common if you have COPD. Wheezing with cough and breathlessness may become worse than usual if you have a chest infection. Sputum usually turns yellow or green during a chest infection.

The phosphatidylcholine in some organs contains relatively high proportions of di-saturated molecular species. For example, it is well known that lung phosphatidylcholine in most if not all animal species studied to date contains a high proportion (50% or more) of dipalmitoylphosphatidylcholine. It appears that this is the main surface-active component, providing alveolar stability by decreasing the surface tension at the alveolar surface to a very low level. Also, the internal lipids of the animal cell nucleus (after the external membrane has been removed) contain a high proportion of desaturated phosphatidylcholine, amounting to 10% of the volume. This is synthesized entirely within the nucleus, unlike phosphatidylinositol for example, and in contrast to other cellular lipids its composition cannot be changed by extreme dietary manipulation. The components of pulmonary surfactant are synthesized in the golgi apparatus of the endoplasmic reticulum of the type II alveolar cell and the secretion is induced by endoplasmic reticulum $Ca_2$ ATP-ase. Infant respiratory distress syndrome (IRDS) is a syndrome caused by lack of surfactant in the lungs of premature infants.

Hypoxemia is to be understood as and refers to low oxygen in the blood which reduces oxygen to the whole body. Hypoxia is abnormally low oxygen content in any tissue or organ caused by injury, disease or drugs. Patients can have hypoxia, without suffering from Hypoxemia. The two are separate diseases. Chronic hypoxemia symptoms also include lung tightness, breathlessness, coughing, low lung capacity and volume. Hypoxemia can be caused by injury to the lungs, caused by lung and sinus diseases and infections, including COPD, chemicals, ozone, lung cancer, and a host of medications that can injure lung cells and decrease the production of lung surfactants. Patients with hypoxemia are usually on oxygen therapy. Hypoxemia is usually defined in terms of reduced partial pressure of oxygen (mm Hg) in arterial blood, but also in terms of reduced content of oxygen (ml oxygen per dl blood) or percentage saturation of hemoglobin (the oxygen binding protein within red blood cells) with oxygen, which is either found singly or in combination. In an acute context, hypoxemia can cause symptoms such as those in respiratory distress. These include breathlessness, an increased rate of breathing, use of the chest and abdominal muscles to breathe, and lip pursing. However, in a chronic context, and if the lungs are not well ventilated generally, this mechanism can result in pulmonary hypertension, overloading the right ventricle of the heart and causing cor pulmonale and right sided heart failure. Polycythemia can also occur. In children, chronic hypoxemia may manifest as delayed growth, neurological development and motor development impairment, and decreases in sleep quality with frequent sleep arousals. Other symptoms of hypoxemia may include cyanosis, and digital clubbing. Severe hypoxemia can lead to respiratory failure. Many patients with lung or sinus diseases experience Hypoxemia. It can be do to the destruction of the alveoli in the lungs or the inadequate production of lung surfactants that enhance oxygen up take. Hypoxemia can occur in patients with and without lung or sinus diseases, in patients with lung infections, heavy metal poisoning with metals like cyanide, and the use of inhaled or non inhaled drugs. It must be noted that there is a difference between people who have transient hypoxemia vs. one that has permanent hypoxemia. The patients respond differently to the inhalation of sodium pyruvate by itself without calcium, phosphate and magnesium. Sodium pyruvate in saline given both orally or by inhalation will increase SaO2 levels in people without hypoxemia. Transient hypoxemia (hypoxic endurance) is a self correcting effect and does not involve lung injury or the inability to synthesize lung surfactants. It occurs in over exercising, mountain climbing etc.

In controlled inhalation studies, patients without hypoxemia, lung injuries or diseases, that produce normal levels of lung surfactants, have shown an increase of SaO2 by an average of 2%-3% when treated with sodium pyruvate in saline especially after exercising. Sodium pyruvate solution was administered in sterile water via a nebulizer to 54 patients and 15 healthy subjects, and the concentrations of nitric oxide exhaled from patients/healthy subjects were measured, as were their oxygen saturation levels. Pyruvate was administered in a nebulizer 5 ml at one time. The pyruvate concentrations were 0.5 mMol, 1.5 mMol, 5.0 mMol and 20 mMol. Each concentration was inhaled once per day. Prior to the inhalation of pyruvate, nitric oxide measurements were taken, as were oxygen saturation levels. Those levels were then taken one hour after the inhalation of the pyruvate solutions. The results showed that the 5 mM and 20 mM solution increased nitric oxide levels by 22% in all subjects. Saline alone did not increase nitric oxide levels or SaO2 in any subject. Oxygen saturation was increased by 3% in these patients.

In controlled inhalation studies, performed as part of this patent, patients with hypoxemia or lung injuries or diseases, and a decreased ability to synthesize lung surfactants, did not show an increase of SaO2 or nitric oxide when treated with inhaled sodium pyruvate in saline alone, and did not show a reduction in lung tightness, dyspnea, coughing or an increase in lung capacity or volume.

Hypoxia in Cancer Cells

Small cell lung cancer (SCLC) is an extremely aggressive disease for which minimal therapeutic improvements have been made over the last few decades. Patients still rely on non-targeted, chemotherapeutic drugs complemented by irradiation. Although initial response is very good, the majority of SCLC patients invariably relapse with therapy-resistant tumors. Despite the link between pathologically low oxygen levels and therapy resistant tumors, hypoxia has gained little attention in the development of novel therapies for SCLC. In contrast, the advantages of targeting hypoxic cells in many other cancer types have been studied extensively. Hypoxia is an important factor in tumor biology and is both a predictive and a prognostic factor in non-small cell lung cancer. The negative effect of low oxygenation on radiation therapy effect has been known for decades, but more recent research has emphasized that hypoxia also has a profound effect on a tumor's aggression and metastatic propensity. Hypoxia is prevalent in small cell lung cancer (SCLC) tumors and leads to cellular adaptations associated with aggressive tumors. Many methods of targeting hypoxia for cancer therapy have been explored; however, this treatment remains relatively under-investigated for SCLC.

Low oxygen levels in cells may be a primary cause of uncontrollable tumor growth in some cancers, according to a new University of Georgia study. The authors' findings run counter to widely accepted beliefs that genetic mutations are responsible for cancer growth. If hypoxia, or low oxygen levels in cells, is proven to be a key driver of certain types of cancer, treatment plans for curing the malignant growth could change in significant ways.

The research team analyzed samples of messenger RNA data—also called transcriptomic data—from seven different cancer types in a publicly available database. They found that long-term lack of oxygen in cells may be a key driver of cancer growth. The study was published in the early online edition of the *Journal of Molecular Cell Biology*.

Previous studies have linked low oxygen levels in cells as a contributing factor in cancer development, but not as the driving force for cancer growth. High incidence rates of cancer around the world cannot be explained by chance genetic mutations alone.

In their study, the researchers analyzed data downloaded from the Stanford Micro-array Database via a software program to detect abnormal gene expression patterns in seven cancers: breast, kidney, liver, lung, ovary, pancreatic and stomach.

They relied on the gene HIF1A as a biomarker of the amount of molecular oxygen in a cell. All seven cancers showed increasing amounts of HIF1A, indicating decreasing oxygen levels in the cancer cells.

Low oxygen levels in a cell interrupt the activity of oxidative phosphorylation, a term for the highly efficient way that cells normally use to convert food to energy. As oxygen decreases, the cells switch to glycolysis to produce their energy units, called ATP. Glycolysis is a drastically less efficient way to obtain energy, and so the cancer cells must work even harder to obtain even more food, specifically glucose, to survive. When oxygen levels dip dangerously low, angiogenesis, or the process of creating new blood vessels, begins. The new blood vessels provide fresh oxygen, thus improving oxygen levels in the cell and tumor and slowing the cancer growth—but only temporarily.

This patent highlights various treatment options available for increasing lung surfactants that are responsible for increasing blood oxygen levels in cancer patients thus targeting hypoxic cells within tumors that could be highly beneficial in the treatment of SCLC.

List of Conditions and Drugs that Impair the Synthesis of Lung Surfactants that Cause Chronic Hypoxemia Hypoxemia is caused by insufficient synthesis of lung surfactants that decreases lung gas exchange, increases lung tightness, coughing and decreases lung capacity. Hypoxemia can be caused by malnutrition, by injury to the lungs, caused by lung and sinus diseases like COPD and asthma, and infections, chemicals, ozone, lung cancer, pulmonary edema, bronchiectasis, bronchiolitis, emphysema, bronchial pneumonia, allergic bronchopneumonia, Allergic Rhinitis, viral pneumonia, Respiratory mucus, nasal congestion, and encephalitis with retained secretions and a host of medications that can injure lung cells that synthesize lung surfactants. Patients with hypoxemia are usually on oxygen therapy.

Medications Administered by Respiratory Therapy that Cause Hypoxemia

The inhaled drugs listed below have some or many of these adverse effects: Hypoxemia, Chest pain, nausea, vomiting, coughing, bronchospasm, headaches, hypoventilation, hypotension, bradycardia, increased infections, blurred vision, mucosal irritation, fatigue, and shortness of breath.

Epinephrine, Racemic Epinephrine (Vaponephrine), Beta-Sympathomimetics:Isoetharine (Bronkosol), Beta 2 agonist:

Metaproterenol (Alupent), Albuterol (Proventil, Ventolin), Terbutaline, (Brethine, Bricanyl) Salmeterol (Serevent), Lev-albuterol (Xopenex), Nonsteroidal Anti-Inflammatory Agents: Cromolyn Sodium (Intal), Nedocromil sodium Tilade, Corticosteroids aerosolized Steroids: a. Dexamethasone (Decadron) b. Beclomethasone (Vanceril, beclovent) c. Triamcinolone (Azmacort) d. Flunisolide (Aerobid) e. Fluticasone propionate (Flovent) a glucocorticoid) f. Budesonide Suspension (Pulmocort), Anticholinergics: Atropine, Ipratropium Bromide (Atrovent.

Mucolytics/Surface Active Agents Acetylcysteine (Mucomyst). Anti-Protozoal Agent:

Pentamidine Isethionate (Nebupent) Combination drugs: Combivent (Ipratropium bromide and albuterol sulfate): Advair Diskus (salmeterol and Flovent), Recombinant Human Deoxy ribonuclease I Solution: Dornase Alfa (Pulmozyme, Anti-Viral Agent:

Virazole (Ribavirin), Antibiotic: Tobramycin (Tobi) Aminoglycoside antibiotic to treat Pseudomonas Aeruginosa, Cancer drugs that increase hypoxemia include 3-Bromopyruvate, 2-Deoxy-D-glucose, Dichloroacetic acid, and Acetylcysteine Antioxidants have been shown to inhibit damage associated with active oxygen species. For example, pyruvate and other alpha ketoacids have been reported to react rapidly and stoichiometrically with hydrogen peroxide to protect cells from cytolytic effects, O'Donnell-Tormey et al., J. Exp. Med., 165, pp. 500-51 4(1987).

U.S. Pat. No. 5,210,098 issued to Nath discloses a method to arrest or prevent acute kidney failure by administration of a non-toxic pyruvate salt to a patient in need of such treatment. The Nath invention provides a therapeutic method comprising administration of an amount of pyruvate salt to a patient experiencing, or in danger of, acute renal failure.

U.S. Pat. Nos. 3,920,835, 3,984,556, 3,988,470, and 4,234,599 all issued to Van Scott et al. disclose methods for treating acne, dandruff, and palmar keratosis, respectively, which consist of applying to the affected area a topical composition comprising from about 1% to about 20% of a lower aliphatic compound containing from two to six carbon atoms selected from the group consisting of alpha-hydroxyacids, alpha-ketoacids and esters thereof, and 3-hydroxybutryic acid in a pharmaceutically acceptable carrier. The aliphatic compounds include pyruvic acid and lactic acid.

Pyruvate has been reported to exert a positive inotropic effect in stunned myocardium, which is a prolonged ventricular dysfunction following brief periods of coronary artery occlusions which does not produce irreversible damage, Mentzer et al., Ann. Surg., 209, pp. 629-633 (1989).

U.S. Pat. Nos. 4,158,057, 4,351,835, 4,415,576, and 4,645,764, all issued to Stanko, disclose methods for preventing the accumulation of fat in the liver of a mammal due to the ingestion of alcohol, for controlling weight in a mammal, for inhibiting body fat while increasing protein concentration in a mammal, and for controlling the deposition of body fat in a living being, respectively.

U.S. Pat. Nos. 5,798,388, 5,939,459, 5,952,384 and 6,623,723 (Katz) pertain to methods for treating inflammation in the lungs and compositions useful in the method. The method comprises contacting the mammalian cells participating in the inflammatory response with an inflammatory mediator. The inflammatory mediator is present in an amount capable of reducing the undesired inflammatory response and is an antioxidant.

U.S. Pat. No. 6,689,810 (Martin) discloses a therapeutic composition for treating pulmonary diseases states in mammals by altering indigenous in vivo levels of nitric oxide. The therapeutic composition consists of pyruvates, pyruvate precursors, α-keto acids having four or more carbon atoms, precursors of α-keto acids having four or more carbons, and the salts thereof. Martin also claimed that all salts of pyruvate were equal.

U.S. Pat. Nos. 8,076,373 and 8,114,907 (Martin) discloses a method for treating pulmonary disease state in mammals by up or down regulating in vivo levels of inflammatory agents (cytokines) in mammalian cells.

While the above therapeutic compositions and methods are reported to inhibit the production and reduce the amount of reactive oxygen intermediates, such as hydrogen peroxide, peroxynitrite or nitric oxide and reduce inflammation, none of the disclosures describe a method and unique formula composition for enhancing the synthesis of lung surfactants, to increase oxygen saturation values (SaO2), decrease coughing, reduce drug side effects which cause hypoxemia, reduce lung tightness, reduce the frequency of lung infections, and enhance drug uptake and efficacy in patients with hypoxemia, with and without lung or sinus diseases. Hypoxemia can be caused by injury to the lungs, caused by lung and sinus diseases and infections, including COPD, chemicals, ozone, lung cancer, and a host of medications that can impair the synthesis of lung surfactants. A number of these patents have claimed that all salts of pyruvate were equal. This patent has demonstrated that not all salts of pyruvate are equal and when tested in humans, the zinc, manganese, aluminum, ammonium, and lithium did not increase FEV-1 or SaO2 levels or reverse Hypoxemia or decrease oxygen radicals as well as sodium pyruvate did. They were in fact irritating.

While the method for treating insufficient lung surfactants that cause hypoxemia in mammalian nasal and sinus cells involved in the disease herein described constitute preferred embodiments of this invention, it is to be understood that the invention is not limited to this precise form or method and that changes may be made therein without departing from the scope of the invention which is defined in the appended claims.

SUMMARY OF THE INVENTION

A sodium pyruvate solution with specific concentrations of calcium, phosphate and magnesium as claimed according to the present invention was superior and was synergistic over our standard sodium pyruvate formula in saline in enhancing the production of surfactants needed to improve lung functions in patients with Hypoxemia and to increase SaO2 values, reduce coughing, reduce lung tightness and reduce lung infections. We have shown that a sodium pyruvate with calcium, phosphate and magnesium formula can reduce the concentrations of inhaled steroids and produce equal or better results.

The present invention utilizes pyruvate delivered in an inhaled sodium pyruvate formula with calcium, phosphate and magnesium (a surfactant enhancer) that will enhance the synthesis lung and sinus surfactants, phospholipids in lung cells to enhance gas exchanges in the lung, increases oxygen saturation levels (SaO2) that facilitates the removal of excess mucus that can block the efficacy of inhaled drugs, thereby enhancing drug uptake and efficacy, while reducing, congestion, breathlessness, coughing, lung tightness, and increasing lung functions. Lung surfactants are mostly phospholipids which are synthesized in the lungs and sinuses. Without these critical phospholipids, in mitochondria, the lung cell would die. Most inhaled drugs cause damage to alveoli and decrease the synthesis of lung surfactants needed to maintain normal lung functions. This therapy consists of contacting the lung or nasal cells with a therapeutically effective amount of the lung surfactant enhancer, alone or in combination with inhaled drugs. Wherein the drugs are selected form antivirals, antihistamines, antibacterials, antifungal, proteins, steroids, cytokines, nonsteroidal anti-inflammatory agents, antioxidants, insulin, nicotine and anticancer drugs wherein the lung surfactant enhancer is selected from the group consisting of pyruvates and pyruvate precursors, various salts of calcium, phosphates and magnesium which enhance the synthesis of lung surfactants to decrease hypoxemia. Previous patents have claimed that pyruvate will work with antibacterials, antivirals, antifungals, antihistamines, proteins, enzymes, hormones, nonsteroidal anti-inflammatories, cytokines, and steroids. The present invention has shown that sodium pyruvate will work with some drugs and not with others and that a inhaled formula of sodium pyruvate, calcium, phosphate and magnesium was superior to sodium pyruvate by itself. This new formula increases SaO2 values, reduced coughing and lung tightness and increased lung capacity in patients with chronic hypoxemia including patients with COPD and asthma and in patients without any lung or sinus diseases. The surfactant enhancer of the present invention may be administered prior to, after and/or with other therapeutic agents. Obviously, numerous modifications and variations of the present invention are possible in the light of the above teachings and the invention is not limited to the example herein. It is therefore understood that within the scope of the appended claims, the invention may be practiced otherwise than as specifically described herein.

The present invention provides novel methods for treating insufficient synthesis of surfactants in patients with non pulmonary and pulmonary diseases or nasal diseases state in mammals with a formula comprising a therapeutically effective amount of a surfactant enhancer which is selected from the group consisting of pyruvates and pyruvate precursors solution containing the correct concentrations of calcium, phosphate and magnesium. Pyruvate provides both the energy in the form of ATP to enhance the synthesis of lung surfactants and as a component of the phospholipids in lung surfactants, calcium and magnesium provide the salts needed by cellular enzymes that produce cellular phospholipids and phosphate is essential component of all phospholipids that makeup all lung and sinus surfactants. Magnesium is also needed for mitochondrial membrane stability and for the production of ATP. This is a unique synergistic formula.

DETAILED DESCRIPTION OF THE INVENTION

The present invention has shown that no inhaled formulas with sodium pyruvate in saline, to date, have been shown to enhance the synthesis of lung and sinus surfactants or increase SaO2 values for the treatment of chronic hypoxemia and that only the combination of sodium pyruvate with calcium, phosphate, and magnesium was synergistic in its ability enhance the synthesis of lung surfactants, that enhance lung oxygen saturation (saO2) and FEV1 values, and reduce lung tightness, breathlessness, coughing, reduce the number of lung or sinus infection, reduce drug side effects that cause hypoxemia. Low SaO2 in humans is called Hypoxemia and can occur in patients with and without lung and sinus diseases, cancer and other conditions that injure lung tissues that will increase mucus production, fatigue, shortness of breath and increased susceptibility to all types of infections. Lung and sinus surfactants mostly phospholipids, cannot be inhaled because they will block oxygen uptake. The salt of calcium can be delivered as calcium phosphate, dicalcium phosphate, and as calcium pyruvate, calcium chloride or calcium citrate or many other forms. The phosphate can be delivered as calcium phosphate, potassium phosphate, magnesium phosphate and in other ways. Magnesium can be delivered as magnesium chloride, magnesium phosphate, or magnesium bicarbonate and magnesium sulfate. The sodium pyruvate formula with calcium, phosphate and magnesium acted synergistically to enhance the synthesis of key cellular phospholipids, thus enhance the synthesis of lung surfactants that enhance lung alveoli functions and oxygen saturation SaO2 values, better than the use of sodium pyruvate or calcium pyruvate formulations by themselves or in combination. Lung surfactants are mostly phospholipids which are synthesized in the cell and mitochondria. Without these critical phospholipids, especially cardiolipin found in mitochondria, the lung cell would die. This three component system includes pyruvate, which become a component of synthesized lung surfactants, and calcium and magnesium provides the salts needed by cellular enzymes that produce cellular phospholipids, magnesium is needed for mitochondrial membrane stability and the production of ATP, and phosphate is essential component of all phospholipids the makeup all lung and sinus surfactants. Magnesium is an essential element in biological systems. Magnesium occurs typically as the $Mg^{2+}$ ion. It is an essential mineral nutrient (i.e., element) for life and is present in every cell type in every organism. For example, ATP (adenosine triphosphate), the main source of energy in cells, must be bound to a magnesium ion in order to be biologically active. What is called ATP is often actually Mg-ATP. As such, magnesium plays a role in the stability of all polyphosphate compounds in the cells, including those associated with the synthesis of DNA and RNA. Over 300 enzymes require the presence of magnesium ions for their catalytic action, including all enzymes utilizing or synthesizing ATP, or those that use other nucleotides to synthesize DNA and RNA. Patients with chronic Hypoxemia have low magnesium levels in the lungs that impair lung enzyme functions.

The inhalation of sodium pyruvate with calcium, phosphate and magnesium (surfactant enhancer) also enhanced drug uptake and efficacy, reducing hypoxemia caused by drugs. The surfactant enhancer formula was superior over the sodium pyruvate saline formulations used in the past without the addition of calcium, phosphate and magnesium. The therapy consist of contacting the lung or nasal cells with a therapeutically effective amount of the lung surfactant enhancer (inhaled sodium pyruvate formula with calcium, phosphate and magnesium), alone or in combination with inhaled and non-inhaled drugs that cause hypoxemia, while enhancing gas exchanges in the lungs. Some inhaled medication reduce the ability of the immune system to fight infections, and some reduce the ability of lungs to synthesize lung surfactants, like steroids, thus the addition of the sodium pyruvate, calcium, phosphate and magnesium formula at higher concentrations will reduce the amount of infections by maintaining a healthier lung environment where oxygen saturations are increased. Wherein the drugs are selected form antivirals, antihistamines, antibacterials, antifungal, proteins, steroids, cytokines, nonsteroidal anti-inflammatory agents, antioxidants, insulin, nicotine and anticancer drugs.

As used herein, the following terms have the given meanings:

The term "injured cell" as used herein refers to a cell which has some or all of the following: (a) injured membranes with insufficient synthesis of lung surfactants that reduce lung gas exchange, that transport through the membranes is diminished and may result in one or more of the following, an increase in toxins and normal cellular wastes inside the cell and/or a decrease in nutrients and other components necessary for cellular repair inside the cell, (b) an increase in concentration of oxygen radicals inside the cell because of the decreased ability of the cell to produce antioxidants and enzymes, and (c) damaged DNA, RNA and ribosomes which must be repaired or replaced before normal cellular functions can be resumed.

The term "pharmaceutically acceptable," such as pharmaceutically acceptable carriers, excipients, etc., refers to pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methane sulfonic acid, oxalic acid, succinic acid, citric acid, malic acid, lactic acid, fumaric acid, and the like. Sample base-addition salts include those derived from calcium, magnesium, ammonium, potassium, sodium, and quaternary ammonium hydroxides, such as for example, tetramethyl-ammonium hydroxide. Chemical modification of a pharmaceutical compound (i.e., drug) into a salt is a technique well known to pharmaceutical chemists to obtain improved physical and chemical stability, hydroscopicity, and solubility of compounds. See. e.g., H. Ansel et. al., Pharmaceutical Dosage Forms and Drug Delivery Systems ($6^{th}$ Ed. 1995) at pp. 196 and 1456-1457.

The term "prodrug" or "precursor" refers to compounds, which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymic regeneration of the parent compound. Regeneration takes place as a consequence of hydrolytic, dissociative, and other reactions not necessarily enzyme mediated. The terms prodrugs, latentiated drugs, and bio-reversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The term "therapeutically effective amount" refers to an amount of a therapeutically effective compound, or a pharmaceutically acceptable salt thereof, which is effective to treat, prevent, alleviate or ameliorate symptoms of a disease.

The diseases listed below will cause oxygen saturation levels (SaO2) to fall, is due to low lung surfactant synthesis and causes Hypoxemia. In smokers 22% suffer from hypoxemia, and in COPD patients 21% have hypoxemia. The pulmonary diseases which cause Hypoxemia and are suitable for treatment by the lung surfactant enhancer of the present invention (sodium pyruvate with calcium, phosphate and magnesium), but are not limited to, acute respiratory distress syndrome (ARDS), acute lung injury, pulmonary fibrosis (idiopathic), Bleomycin induced pulmonary fibrosis, mechanical ventilator induced lung injury, lung transplantation-induced acute graft dysfunction and bronchiolitis obliterans after lung transplantation, bronchial asthma, acute bronchitis, emphysema, chronic obstructive emphysema, chronic obstructive pulmonary disease, centrilobular emphysema, panacinar emphysema, chronic obstructive bronchitis, smoker's disease, reactive airway disease, cystic fibrosis, black lung disease, bronchiectasis, acquired bronchiectasis, kartaagener's syndrome, acelectasis, acute atelectasis, chronic acelectasis, pneumonia, essential thrombocythemia, legionnaire's disease, psittacosis, fibrogenic dust disease, hypersensitivity diseases of the lung, idiopathic infiltrative diseases of the lungs, chronic obstructive pulmonary disorder, adult respiratory distress syndrome, pulmonary tumors, pulmonary hypertension, and diseases caused by organic dust, cyanide poisoning, nicotine, insulin, irritant gases, Alzheimer's, nasal diseases like allergic rhinitis, sinusitis and chemicals like Cyanide, ozone, lung or sinus infections, inhaled cancer drugs or inhaled drugs, cancer, sleep apnea, and Migraines. Preferred disease states are cystic fibrosis, bronchial asthma, allergic rhinitis, sinusitis, Bleomycin (doxorubicin) injury, chronic obstructive pulmonary disease, interstitial lung disease, lung cancer and migraines.

The pulmonary tumors suitable for treatment by the surfactant enhancer of the present invention include, but are not limited to, epidermoid (squamous cell) carcinoma, small cell (oat cell) carcinoma, adenocarcinoma, and large cell (anaplastic) carcinoma.

The surfactant enhancer in the present invention is pyruvates and pyruvate precursors with the addition of calcium, phosphate and magnesium. Non-limiting illustrative examples of pyruvates include pyruvic acid, sodium pyruvate, potassium pyruvate, magnesium pyruvate, calcium pyruvate, zinc pyruvate, manganese pyruvate, aluminum pyruvate, ammonium pyruvate, lithium pyruvate, and mixtures thereof. Non-limiting illustrative examples of pyruvate precursors include ethyl pyruvate, methyl pyruvate, pyruvyl-glycine, pyruvyl-alanine, pyruvyl-cysteine, pyruvyl-leucine, pyruvyl-valine, pyruvyl-isoleucine, pyruvyl-phenylalanine, pyruvamide, salts of pyruvic acid, and mixtures thereof, with calcium, phosphate and magnesium.

The amount of the surfactant enhancer present in the therapeutic compositions of the present invention is a therapeutically effective amount. A therapeutically effective amount of the surfactant enhancer is that amount of the surfactant enhancer necessary to increase the synthesis of lung phospholipids to treat Hypoxemia. The exact amount of surfactant enhancer is a matter of preference subject to such factors as the type of surfactant enhancer being employed, the type of condition being treated as well as the other ingredients in the composition. The exact amount of surfactant enhancer will also be determined by whether the pulmonary disease is infected or uninfected. In general, the dosage of the surfactant enhancer may range from about 0.00001 mg to about 1 gram, preferably from about 0.001 mg to about 0.8 gram, and more preferably from about 0.01 mg to about 0.6 gram.

In many cases, pulmonary diseases produce infections that these surfactant enhancers can treat. Such infections may be bacterial, viral, or fungal. The surfactant enhancer may be inhaled first to regulate inflammatory agents followed by inhalation or oral administration of a therapeutic agent. The therapeutic agent may be administered prior to, concomitantly with, or after administration of the inflammatory regulator. The therapeutic agent may be selected from the group consisting of antibacterials, antivirals, antifungals, antitumors, antihistamines, proteins, enzymes, hormones, nonsteroidal anti-inflammatories, cytokines, nicotine, insulin, and steroids.

The antibacterial agents which may be employed in the therapeutic compositions may be selected from a wide variety of water-soluble and water-insoluble drugs, and their acid addition or metallic salts, useful for treating pulmonary diseases. Both organic and inorganic salts may be used provided the antibacterial agent maintains its medicament value. The antibacterial agents may be selected from a wide range of therapeutic agents and mixtures of therapeutic agents, which may be administered in sustained release or prolonged action form. Nonlimiting illustrative specific examples of antibacterial agents include bismuth containing compounds, sulfonamides; nitrofurans, metronidazole, tinidazole, nimorazole, benzoic acid; aminoglycosides, macrolides, penicillin's, polypeptides, tetracyclines, cephalosporins, chloramphenicol, and clindamycin. Preferably, the antibacterial agent is selected from the group consisting of bismuth containing compounds, such as, without limitation, bismuth aluminate, bismuth subcitrate, bismuth subgalate, bismuth subsalicylate, and mixtures thereof; the sulfonamides; the nitrofurans, such as nitrofurazone, nitrofurantoin, and furazolidone; and miscellaneous antibacterials such as metronidazole, tinidazole, nimorazole, and benzoic acid; and antibiotics, including the aminoglycosides, such as gentamycin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bacitracin and polymyxin; the tetracyclines, such as tetracycline, chlortetracycline, oxytetracycline, and doxycycline; the cephalosporins, such as cephalexin and cephalothin; and miscellaneous antibiotics, such as chloramphenicol, and clindamycin. More preferably, the antibacterial agent is selected from the group consisting of bismuth aluminate, bismuth subcitrate, bismuth subgalate, bismuth subsalicylate, sulfonamides, nitrofurazone, nitrofurantoin, furazolidone, metronidazole, tinidazole, nimorazole, benzoic acid, gentamycin, neomycin, kanamycin, streptomycin, erythromycin, clindamycin, rifamycin, penicillin G, penicillin V, Ampicillin amoxicillin, bacitracin, polymyxin, tetracycline, chlortetracycline, oxytetracycline, doxycycline, cephalexin, cephalothin, chloramphenicol, clindamycin, Bactorban (Mupirocin), Tobramycin, Pentamidine isethionate, Vancomycin, benzalkonium chloride.

The amount of antibacterial agent which may be employed in the therapeutic compositions of the present invention may vary depending upon the therapeutic dosage recommended or permitted for the particular antibacterial agent. In general, the amount of antibacterial agent present is the ordinary dosage required to obtain the desired result. Such dosages are known to the skilled practitioner in the medical arts and are not a part of the present invention. In a preferred embodiment, the antibacterial agent in the therapeutic composition is present in an amount from about 0.01% to about 10%, preferably from about 0.1% to about 5%, and more preferably from about 1% to about 3%, by weight.

The antiviral agents which may be employed in the therapeutic compositions may be selected from a wide variety of water-soluble and water-insoluble drugs, and their acid addition or metallic salts, useful for treating pulmonary diseases. Both organic and inorganic salts may be used provided the antiviral agent maintains its medicament value. The antiviral agents may be selected from a wide range of therapeutic agents and mixtures of therapeutic agents, which may be administered in sustained release or prolonged action form. Nonlimiting illustrative categories of such antiviral agents include RNA synthesis inhibitors, protein synthesis inhibitors, immunostimulating agents, protease inhibitors, and cytokines. Nonlimiting illustrative specific examples of such antiviral agents include the following medicaments. Acyclovir with inhibitory activity against human herpes viruses including herpes simplex types 1 (HSV-1) and 2 (HSV-2), varicella-zoster virus (VZV), Epstein-Barr virus (EBV), and cytomegalovirus (CMV). Foscarnet sodium is an organic analogue of inorganic pyrophosphate that inhibits replication of all known herpes viruses in vitro including cytomegalovirus (CMV), herpes simplex virus types 1 and 2 (HSV-1, HSV-2), human herpes virus 6 (HHV-6), Epstein-Barr virus (EBV), and varicella-zoster virus (VZV).

Ribavirin has antiviral inhibitory activity in vitro against respiratory syncytial virus, influenza virus, and herpes simplex virus. Vidarabine possesses in vitro and in vivo antiviral activity against Herpes simplex virus types 1 and 2 (HSV-1 and HSV-2), and in vitro activity against varicella-zoster virus (VZV). Ganciclovir inhibits replication of herpes viruses both in vitro and in vivo. Sensitive human viruses include cytomegalovirus (CMV), herpes simplex virus-1 and -2 (HSV-1, HSV-2), Epstein-Barr virus (EBV), and varicella zoster virus (VZV). Zidovudine is an inhibitor of the in vitro replication of some retroviruses including HIV (also known as HTLV III, LAV, or ARV). Phenol (carbolic acid) is a topical antiviral, anesthetic, antiseptic, and antipruritic drug. Amantadine hydrochloride (1-adamantanamine hydrochloride, SYMMETREL®) has pharmacological actions as both an anti-Parkinson and an antiviral drug against influenza A. Interferon $\alpha$n3 (human leukocyte derived, ALFERON®) $\alpha$ proteins for use by injection. Interferons are naturally occurring proteins with both antiviral and antiproliferative properties. Interferon $\alpha$-2a (recombinant, ROFERON-A®). The mechanism by which Interferon $\alpha$-2a, recombinant, exerts antitumor or antiviral activity is not clearly understood. Oseltamivir ((3R,4R,5S)-4-acetylamino-5-amino-3-(1-ethylpropoxy)-1-cyclohexene-1-carboxylic acid ethyl ester, TAMIFLU®) is a is an antiviral drug that is used in the treatment and prophylaxis of both influenza virus A and Influenza virus B. Zanamivir. Preferred antiviral agents to be employed may be selected from the group consisting of acyclovir, foscarnet sodium, Ribavirin, vidarabine, Ganciclovir sodium, zidovudine, phenol, amantadine hydrochloride, and interferon $\alpha$-n3, interferon $\alpha$-2a, and Oseltamivir. In a preferred embodiment, the antiviral agent is selected from the group consisting of acyclovir, foscarnet sodium, Zanamivir, Ribavirin, vidarabine, valacydvir, famiclour, Tenofovir Viread and Ganciclovir sodium. In a more preferred embodiment, the antiviral agent is acyclovir.

The amount of antiviral agent which may be employed in the therapeutic compositions of the present invention may vary depending upon the therapeutic dosage recommended or permitted for the particular antiviral agent. In general, the amount of antiviral agent present is the ordinary dosage required to obtain the desired result. Such dosages are known to the skilled practitioner in the medical arts and are not a part of the present invention. In a preferred embodiment, the antiviral agent in the therapeutic composition is present in an amount from about 0.1% to about 20%, preferably from about 1% to about 10%, and more preferably from about 2% to about 7%, by weight.

The antifungal agents which may be employed in the therapeutic compositions may be selected from a wide variety of water-soluble and water-insoluble drugs, and their acid addition or metallic salts, useful for treating pulmonary diseases. Both organic and inorganic salts may be used provided the antifungal agent maintains its medicament value. The antifungal agents may be selected from a wide range of therapeutic agents and mixtures of therapeutic agents, which may be administered in sustained release or prolonged action form. Nonlimiting illustrative specific examples of antifungal agents include the following medicaments: miconazole, clotrimazole, tioconazole, terconazole, povidone-iodine, and butoconazole. Other antifungal agents are lactic acid and sorbic acid. Preferred antifungal agents are miconazole and clotrimazole.

The amount of antifungal agent, which may be employed in the therapeutic compositions of the present invention may vary depending upon the therapeutic dosage recommended or permitted for the particular antifungal agent. In general, the amount of antifungal agent present is the ordinary dosage required to obtain the desired result. Such dosages are known to the skilled practitioner in the medical arts and are not a part of the present invention. In a preferred embodiment, the antifungal agent in the therapeutic composition is present in an amount from about 0.05% to about 10%, preferably from about 0.1% to about 5%, and more preferably from about 0.2% to about 4%, by weight.

The antitumor agents which may be employed in the therapeutic compositions may be selected from a wide variety of water-soluble and water-insoluble drugs, and their acid addition or metallic salts, useful for treating pulmonary diseases. Both organic and inorganic salts may be used provided the antitumor agent maintains its medicament value. The antitumor agents may be selected from a wide range of therapeutic agents and mixtures of therapeutic agents, which may be administered in sustained release or prolonged action form. Nonlimiting illustrative specific examples include anti-metabolites, antibiotics, plant products, hormones, and other miscellaneous chemotherapeutic agents. Chemically reactive drugs having nonspecific action include alkylating agents and N-alkyl-N-nitroso compounds. Examples of alkylating agents include nitrogen mustards, aziridines (ethylenimines), sulfonic acid esters, and epoxides. Anti-metabolites are compounds that interfere with the formation or utilization of a normal cellular metabolite and include amino acid antagonists, vitamin and coenzyme antagonists, and antagonists of metabolites involved in nucleic acid synthesis such as glutamine antagonists, folic acid antagonists, pyrimidine antagonists, and purine antagonists. Antibiotics are compounds produced by microorganisms that have the ability to inhibit the growth of other organisms and include actinomycins and related antibiotics, glutarimide antibiotics, sarkomycin, fumagillin, streptonigrin, tenuazonic acid, actinogan, peptinogan, and anthracyclic antibiotics such as doxorubicin. Plant products include colchicine, podophyllotoxin, and vinca alkaloids. Hormones include those steroids used in breast and prostate cancer and corticosteroids used in leukemia and lymphomas. Other miscellaneous chemotherapeutic agents include urethane, hydroxyurea, and related compounds; thiosemicarbazones and related compounds; phthalanilide and related compounds; and triazene's and hydrazines, 3-Bromopyruvate, 2-Deoxy-D glucose, Dichloroacetic acid. The anticancer agent may also be a monoclonal antibody or the use of X-rays. In a preferred embodiment, the anticancer agent is an antibiotic. In a more preferred embodiment, the anticancer agent is doxorubicin. In a most preferred embodiment, the anticancer agent is doxorubicin. Lung Cancer—Medications Chemotherapy is called a systemic treatment because the medicines enter your bloodstream, travel through your body, and kill cancer cells both inside and outside the lung area. Some chemotherapy drugs are taken by mouth (orally), while others are injected into a vein (intravenous, or IV). Some of the more common chemotherapy medicines used for lung cancer includes the following: Bevacizumab, Carboplatin, Cisplatin, Crizotinib, Docetaxel, Erlotinib, Etoposide, Gemcitabine, Irinotecan, Paclitaxel, Pemetrexed Vinorelbine. Most chemotherapy causes some side effects, including destruction of mitochondria which causes an insufficient synthesis of lung surfactants that lead to hypoxemia and reduces the ability of cancer cells to undergo Apoptosis.

The amount of antitumor agent, which may be employed in the therapeutic compositions of the present invention may vary depending upon the therapeutic dosage recommended or permitted for the particular antitumor agent. In general, the amount of antitumor agent present is the ordinary dosage required to obtain the desired result. Such dosages are known to the skilled practitioner in the medical arts and are not a part of the present invention. In a preferred embodiment, the antitumor agent in the therapeutic composition is present in an amount from about 1% to about 50%, preferably from about 10% to about 30%, and more preferably from about 20% to about 25%, by weight.

The carrier composition is selected from the group consisting of tablets, capsules, liquids, isotonic liquids, isotonic media, enteric tablets and capsules, parenteral, topicals, creams, gels, ointments, chewing gums, confections and the like. The favored method of delivery is through inhalation by mouth or sinuses.

Obviously, numerous modifications and variations of the present invention are possible in the light of the above teachings and the invention is not limited to the examples herein. It is therefore understood that within the scope of the appended claims, the invention may be practiced otherwise than as specifically described herein.

Throughout this application, various publications have been referenced. The disclosures in these publications are incorporated herein by reference in order to more fully describe the state of the art.

The compounds of the present invention can be prepared according to the examples set out below. The examples are presented for purposes of demonstrating, but not limiting, the preparation of the compounds and compositions of this invention.

Example 1

Sodium Pyruvate Formula Containing Calcium, Phosphate and Magnesium

All previous studies using pyruvate to treat Allergic Rhinitis, Asthmatic and COPD patients used only the sodium salt form of pyruvic acid in saline. The drug products that were tested in the six Phase I/II clinical trial were differing concentrations of sodium pyruvate dissolved in 0.9% sodium chloride solution (Saline). These drug products contained 0.5 mM, 1.5 mM, or 5.0 mM of sodium pyruvate in physiological saline. They were administered to normal volunteers and COPD and asthmatics by inhalation therapy.

Even though other salts of pyruvic acid like calcium, potassium or zinc etc have been suggested, no one to date has evaluated the different salts individually or in combination for their ability to enhance lung function and reduce lung tightness due to low surfactant production and help in mucus removal that can inhibit drug efficacy. Removal of mucus will increase the efficacy of the pyruvate membrane transport system. Various sodium pyruvate saline solutions were evaluated in the lungs for their ability to enhance FEV1 values. 5 ml 0.5 mM solutions to 5 mM solutions of sodium pyruvate in saline were evaluated in Asthmatic and COPD patients and the 5 ml of the 0.5 mM solution produced the best results in increasing FEV1 values over 12% and reducing nitric oxide by 19.2%. The products that were tested in the clinical trials were differing concentrations of sodium pyruvate dissolved in 0.9% sodium chloride solution. These drug products contained 0.5 mM, 1.5 mM, or 5.0 mM (275, 825, and 2750 µg) of sodium pyruvate, respectively delivered per dose per day. Of these, a 5 mL dose of 0.5 mM sodium pyruvate dissolved in 0.9% sodium chloride solution proved to be the concentration and dosage of choice in past clinical studies. Various investigators including Katz discovered that the higher concentrations of sodium pyruvate 1.5 mM, or 5.0 mM (825, and 2750 µg) in saline did not increase FEV1 values.

Blood levels of the various salts mg/liter are 3220 mg for Sodium, 200 mg for potassium, 27 mg for magnesium, 70 mg for calcium, 1.1 mg for zinc, 0.02 mg for manganese, 6 mg for lithium, 0.03 mg for aluminum, 0.06 mg for ammonium and 0.36 mg for phosphate. To evaluate the irritation or toxicity levels of these elements 5 mls of 0.5 mM solution of each salt of pyruvate, was tested against the standard 5 mls of the 0.5 mM saline solution of sodium pyruvate that was shown to be non toxic in humans and animal studies. In fact, in rat studies, 100× concentrations of the 5 mM sodium pyruvate was tested and shown not to have any irritation or toxicity. Using 5 mls of a 0.5 mM pyruvate inhalation solution of each salt in COPD and asthmatic patients, the use of potassium pyruvate, magnesium pyruvate, calcium pyruvate, zinc pyruvate, manganese pyruvate, lithium pyruvate, aluminum pyruvate, and ammonium pyruvate were evaluated. Potassium pyruvate, produced lower FEV1 results in COPD patients than the sodium pyruvate solution did (FEV1 of 12% or higher). The calcium pyruvate and magnesium pyruvate increased FEV1 values to 10%. The zinc pyruvate, manganese pyruvate, aluminum pyruvate, ammonium pyruvate, and lithium pyruvate did produce slight increases in FEV1 of around 4-6% but did not reduce nitric oxide and did not achieve the results that sodium pyruvate produced, and they were irritating. The zinc pyruvate increased nitric oxide levels by 10% instead of reducing it, acting in the opposite direction that sodium pyruvate did. See table I. A metal taste to these solutions was described by the inhalers. The amount of the salts delivered in the 5 ml's of the 0.5 mM pyruvate solutions were compared to the amounts of the salts in 5 ml's of human blood. The sodium, potassium, and calcium, pyruvates were all under amounts found in human blood. The delivered zinc in this solution (5 ml of a 0.5 mM) was 12× blood levels, the magnesium was 4× blood levels, the manganese was 370× blood levels, aluminum was 61× times blood levels, the ammonium was 53× times blood levels, and lithium was 5× blood levels. These solutions were also evaluated in the nasal cavities and were less irritating than in the lungs except, the ammonium and lithium pyruvate was even more irritating than its use in the lungs. The use of these elements at these levels proved, proved that one cannot assume that all the salts of pyruvate are equal in efficacy or in irritation when compared to the sodium salt see table I. Even though the use of some of these salts of pyruvic acid showed similar FEV1 results, the others did not. The use of some of these salts over time may have a negative effect. The sodium salt of pyruvate when tested at higher levels in humans like the 5 ml of the 5 mM was 59 times lower than sodium in 5 ml's of blood, the calcium was 1.5× times lower, the potassium was 3.2× times lower than 5 ml's of blood, thus they were well within the safe levels needed to deliver the pyruvate. In small doses the salts of zinc or manganese can be used to increase and up regulate the immune system cytokines to fight infections, rather than their use as an anti-inflammatory agent that increases lung functions and FEV1 values. Lithium pyruvate had the unexpected result of acting as a bronchial dilator where as the other salts were weak or nonexistent as a bronchial dilator.

When the sodium pyruvate saline solution (0.5 mM, 0.274 mg) was balanced with the salt of calcium pyruvate or calcium chloride to the concentrations of the salts found in blood (formula was 97% sodium pyruvate, 3% calcium pyruvate or 3% calcium chloride), it produced equal results in FEV1 values when compared to the original sodium pyruvate formula tested in the COPD patients. This formula can also be made by adding 3% calcium phosphate or dicalcium phosphate to the standard 0.5 mM to 30 mM sodium pyruvate saline solution see Table I.

The sodium pyruvate formula with the calcium, phosphate and magnesium was significantly superior to any other formula Tested I-II. In previous studies, sodium pyruvate solutions of 5 to 20 mM did not increase FEV1 values and did increase nitric oxide levels significantly to 19%. The FEV1 values increase to 16% for the sodium pyruvate calcium, phosphate and magnesium formula (5 mM solution) and nitric oxide increased by 70%, far different results than the 5-20 mM straight sodium pyruvate formula without the calcium, phosphate and magnesium see table II. It was also reported by the patients that the sodium pyruvate calcium, phosphate and magnesium formula was the best formula to reduce lung tightness coughing and mucus. The addition of all the other salts of pyruvate including zinc, lithium, magnesium, aluminum, ammonium, or manganese even at blood levels concentrations individually, gave the formula a metal taste and was not preferred by the patients that inhaled it see table II.

TABLE I

Comparison of various inhaled salts of pyruvate in 5 ml's of a 0.5 mM solution in patients with lung diseases including COPD. Overall rating was 1-10 with 1 being the most negative and 10 being the best result

| Various Salts of pyruvate in physiological saline | Increased in FEV-1% lung function | Percentage decrease or increase of Nitric Oxide over baseline | Irritation | Relief of congestion, coughing and lung tightness | Percentage increase in SaO2 over baseline | Overall Rating 1-10 |
|---|---|---|---|---|---|---|
| Sodium | 13.0 | −19.0 | none | 5 | 0.5 | 8 |
| Calcium | 10.0 | −18 | None | 5 | no | 7 |
| Potassium | 8.0 | −14 | None | 5 | no | 7 |
| Magnesium | 12.0 | −2.0 | None | 6 | no | 7 |
| Zinc | 8.0 | +10 | Yes | 4 | No | 4 |
| Manganese | 3.0 | −2.0 | Yes | 4 | No | 3 |
| Lithium | 1.0 | +6.0 | Yes | 2 | No | 2 |
| Aluminum | 0 | +8.0 | Yes | 1 | No | 3 |
| Ammonium | 0 | +5.0 | Yes | 1 | No | 1 |
| Potassium Phosphate | 0 | 0 | Slight | 4 | No | 3 |
| sodium pyruvate & calcium pyruvate | 12.2 | −18 | None | 6 | No | 8 |
| sodium pyruvate & calcium pyruvate & magnesium | 11.8 | −14 | None | 6 | No | 8 |
| calcium & Phosphate & magnesium | 0 | 0 | None | 1 | No | 2 |
| Sodium Pyruvate & calcium & Phosphate & magnesium | 16 | −28 | None | 9 | 5% | 10 |
| physiological Saline 0.9% | 0 | 0 | None | 0 | 0 | 5 |
| Pyruvyl-cysteine | 11 | 0 | None | 5 | 0 | 8 |
| N-acetylcysteine | 6 | 0 | None | 8 | 0 | 7 |

TABLE II

Comparison of various inhaled salts of pyruvate in 5 ml's of a 5 mM solution in patients with lung diseases including COPD. Overall rating was 1-10 with 1 being the most negative and 10 being the best result

| Various Salts of pyruvate in saline | Increased in FEV-1% | Percentage increase of Nitric Oxide over base line | Irritation | Relief of congestion, coughing and lung tightness | Percentage Increase in SaO2 over baseline | Overall Rating 1-10 |
|---|---|---|---|---|---|---|
| Sodium | 2.0 | 19.0 | none | 5 | 1 | 8 |
| Calcium | 1.0 | 17.0 | None | 5 | 1 | 7 |
| Potassium | 2.1 | 25.0 | None | 5 | no | 7 |
| Magnesium | 2.0 | 5.1 | None | 6 | no | 7 |
| Zinc | 1.0 | 22.0 | Yes | 4 | No | 3 |
| Manganese | 3.0 | 25.0 | Yes | 4 | No | 3 |
| Lithium | 1.0 | 28.0 | Yes | 2 | No | 2 |
| Aluminum | 0 | 15.0 | Yes | 1 | No | 4 |
| Ammonium | 0 | 35.0 | Yes | 1 | No | 1 |
| Potassium Phosphate | 0 | 0 | Slight | 4 | No | 3 |
| sodium & calcium pyruvate | 2.2 | 16 | None | 6 | No | 8 |
| sodium & calcium pyruvate & magnesium | 3.4 | 15 | None | 6 | No | 8 |
| calcium & Phosphate & magnesium | 0 | 0 | None | 1 | No | 2 |

TABLE II-continued

Comparison of various inhaled salts of pyruvate in 5 ml's of a 5 mM solution in patients with lung diseases including COPD. Overall rating was 1-10 with 1 being the most negative and 10 being the best result

| Various Salts of pyruvate in saline | Increased in FEV-1% | Percentage increase of Nitric Oxide over base line | Irritation | Relief of congestion, coughing and lung tightness | Percentage Increase in SaO2 over baseline | Overall Rating 1-10 |
|---|---|---|---|---|---|---|
| Sodium Pyruvate & calcium & Phosphate & magnesium | 16 | 70 | None | 9 | 5% | 10 |
| physiological Saline 0.9% | 0 | 0 | 0 | 0 | 0 | 5 |
| Pyruvyl-cysteine | 5 | 1 | Slight | 8 | 0 | 8 |
| N-acetylcysteine | 2 | 1 | yes | 7 | 0 | 7 |

Example II

Effect of CO2 Concentration on Phospholipid Metabolism in the Isolated Perfused Rat Lung. In Hypoxemia CO2 Levels Rise as $SaO_2$ Levels Decline Studies have been carried out on the incorporation of [U-(14)C]glucose, [2-(14)C]pyruvate, [2-(14)C]acetate, and [1-(14)C]-palmitate into the phospholipids of the isolated perfused rat lung in the presence of either 6 or 45 mm total CO(2) concentration in the perfusion medium. Incorporation of [U-(14)C]glucose into total phospholipid and into the phosphatidylcholine fraction was increased 19-53% over the 2-hr perfusion period in lungs perfused with medium containing 45 as compared with 6 mm CO(2). The incorporation of [2-(14)C]acetate, [2-(14)C]-pyruvate, and [1-(14)C] palmitate was not affected by the change in medium CO(2) concentration and Incorporation of [U-(14)C] pyruvate into total phospholipid and into the phosphatidylcholine fraction was increased 1-3% over the 2-hr perfusion period in lungs perfused. Increased incorporation of [U-(14)C]glucose combined with a shift toward greater incorporation into the fatty acids of the phosphatidylcholine fraction produced a maximum increase of 90% in [U-(14)C]glucose incorporation into the fatty acids of phosphatidylcholine after 2 hr of perfusion in the presence of medium containing 45 mm CO(2) as compared with 6 mm CO$_{(2)}$. 45 mm CO2 increases hypoxemia. The increase in medium CO(2) concentration produced as much as a 150% increase in [U-(14)C]glucose incorporation into palmitate derived from the phosphatidylcholine fraction. The results provide evidence that glucose functions as an important precursor of palmitate in the phosphatidylcholine fraction of lung phospholipids and that the CO(2) concentration of the perfusion medium affects the incorporation of glucose into palmitate, whereas in hypoxemia states sodium pyruvate is not incorporated into lung surfactants.

The combination of sodium pyruvate and calcium, phosphate and magnesium was synergistic in its ability to increase the incorporation of pyruvate into lung surfactant phospholipids. It enhanced surfactant production, pyruvate uptake and mucus removal. The production of phospholipids that make up the lung surfactants, needed to enhance alveoli function, need trace minerals and salts to be synthesized. The components of pulmonary surfactant are synthesized in the Golgi apparatus of the endoplasmic reticulum of the type II alveolar cell and the secretion is induced by endoplasmic reticulum Ca2 ATPase. The addition of calcium, phosphate and magnesium, with sodium pyruvate, enhanced the production of the surfactants. In previous studies with rat lungs, [2-(14) c]-pyruvate without the addition of calcium, phosphate and magnesium, was not incorporated into lung surfactants under high CO2 levels which produces hypoxemia. In isolated perfused rat lungs, using [2-(14)C] labeled pyruvate: lung surfactant analysis clearly showed that the sodium pyruvate, calcium, phosphate and magnesium formula increased the production of surfactants over all other formulations with just sodium pyruvate in saline alone. It was also discovered that 50% of the radioactive pyruvate with the addition of calcium, phosphate and magnesium, was incorporated into phosphatidylcholine the main lung surfactant with 45 mm CO2 concentrations. In short, calcium, phosphate and magnesium is needed by the enzyme systems to synthesize lung surfactants, while phosphate provides some of the building components needed to make surfactants, or to increase the synthesis of surfactants and, thus decrease hypoxemia. Inhalation studies with just [2-(14)C] labeled sodium pyruvate without calcium, phosphate and magnesium, showed that pyruvate was converted in the lungs or sinuses to acetate and carbon dioxide and higher levels of pyruvate increased the synthesis of nitric oxide and was not incorporated into synthesized phospholipids. In patients with excess mucus, the formula of sodium pyruvate and calcium, phosphate and magnesium helped facilitate mucus removal, by providing the energy and nutrients needed by the cilia in the nasal and lung passages to remove the mucus. This formula was evaluated in patients with excess mucus. See tables I-III.

TABLE III

Comparison of various 5 ml's of 5 mM sodium pyruvate saline formulas in patients with hypoxemia with and without lung diseases. Overall rating was 1-10 with 1 being the most negative and 10 being the best result

| Various Salts of pyruvate in saline | Percentage Increase in FEV-1 over baseline | Percentage increase of Nitric Oxide over baseline | Relief of Congestion and lung tightness 1-10 | Relief of coughing percentage decrease in four hours | Percentage Increase in SaO2 over baseline | Overall Rating 1-10 |
|---|---|---|---|---|---|---|
| Sodium pyruvate | 4.0 | 18.0% | 5 | 15 | 0 | 7 |
| sodium pyruvate & calcium pyruvate | 4.0 | 19.0% | 5 | 16 | 0 | 7 |
| sodium pyruvate & calcium & phosphate | 3.0 | 18% | 5 | 22 | 0 | 7 |
| calcium & Phosphate & magnesium | 0 | 0 | 1 | 1 | 0 | 3 |
| Sodium Pyruvate & calcium & Phosphate & magnesium | 15.2 | 80% | 9 | 48 | 6% | 10 |
| physiological Saline | 0 | 2% | 5 | 2 | 0 | 3 |
| Sodium Pyruvate & calcium & Phosphate & Magnesium + N-acetylcysteine | 14.9 | 112% | 9 | 44 | 5% | 9 |
| Sodium pyruvate + N-Acetylcysteine | 4 | 15% | 7 | 12 | 1 | 8 |

Example III

Inhalation Formulation

Numerous inhaled saline formulas have been used alone or as part of a solution to carry drugs into the lungs to treat lung diseases, cancer, infections etc. To date, none of these FDA approved saline inhalation formulas, have been shown to enhance the synthesis of lung surfactants, treat hypoxemia by increasing SaO2 levels, while increasing the synthesis of nitric oxide. The following saline formulas were assessed: physiological saline, lactated Ringers, acetated Ringers, ethyl pyruvate Ringers, Phosphate buffered saline, TRIS buffered saline, Hepes buffered saline, Citrate saline, Hanks balanced salt solution, Eagles balanced salt solution, Geys balanced salt solution, aerosolized sea salt, and Earls balanced salt solution. All these formulas are the same in that they all use sodium chloride at 8-9 grams per liter or higher and when tested in patients with various sinus or lung diseases including COPD patients with hypoxemia, none of these formula increased SaO2 levels or decreased lung tightness, coughing or increased lung capacity. None of these formula have all of the correct ingredients or the correct ratios of Sodium pyruvate, calcium, phosphate, or magnesium. Most of these formulas also contain glucose that inhibits the incorporation of pyruvate into phospholipids. When the correct concentrations and ratios of sodium pyruvate with calcium, magnesium and phosphate, are added, these saline formulas increased SaO2 levels, decreased lung tightness, coughing and increased lung capacity in patients with lung damage. Inhalation of sea salt aerosol (9 grams in one liter of distilled water) is clinically proven to cleans the respiratory system of the body and speeds up the elimination of toxins. Salt therapy for Chronic Obstructive Pulmonary Disease (COPD) is a natural and effective treatment for a number of health issues, including emphysema and bronchitis that relate to the lungs and that are grouped together under the banner of Chronic Obstructive Pulmonary Disease. Salt therapy is 100% natural, safe and drug-free, providing effective long-term relief. Sodium and chloride are the most abundant ions in sea salt, representing about 33 and 50.9 percent of total minerals, respectively. Potassium is another important macro-mineral that works with chloride to help regulate acid levels in your body. Sea salt contains also contains Calcium and magnesium. Sea salt can also contain numerous trace elements. Trace minerals you may find in sea salt include, bromine, boron, zinc, iron, manganese, copper and silicon. What's missing in sea salt is the correct composition of ingredients, with the correct concentrations and ratios of sodium pyruvate, calcium, magnesium and phosphate. When tested by itself, in hundreds of published clinical studies, or with the addition of sodium pyruvate, sea salt did not increase the synthesis of lung phospholipids, nor decrease hypoxemia, decrease lung tightness or increase lung capacity or SaO2 levels. When the correct composition of ingredients with the correct concentrations and ratios of sodium pyruvate, calcium, phosphate, and magnesium were added to sea salt, the synthesis of lung surfactants increased, lung capacity increased, lung tightness decreased and hypoxemia decreased.

20 mM Sodium Pyruvate Formula for Inhalation:

To one liter of purified water, add 0.65% Sodium Chloride (contains 6.5 grams of NaCl), add 0.22% (2.2 grams) of sodium pyruvate, 0.05% calcium chloride (0.05 grams), 0.11% of magnesium chloride (0.11 grams), 0.03% potassium phosphate (0.03 grams). A 20 mM formula would contain 2.2 grams of sodium pyruvate. A 0.5 mM solution would contain 0.055 grams of sodium pyruvate. 5 ml's of these formulations, can be inhaled by nebulization or deliver nasally. A second approached tried with the same effect was to first have the patients inhale 5 ml's of physiological saline with the addition of 0.05% calcium chloride (0.05 grams), 0.11% of magnesium chloride (0.11 grams), and 0.03% potassium phosphate (0.03 grams) per liter followed by the inhalation of sodium pyruvate in physiological saline one hour later.

This formula has many modifications to deliver the correct amount of pyruvate, calcium, phosphate and magnesium. The concentration of sodium chloride can be lowered to product a hypotonic saline formula, or increased above 0.9% to produce a hypertonic saline solution. These modifications to sodium chloride will not effect the efficacy of the surfactant enhancer to increase the synthesis of lung surfactants. Phosphate can be delivered as calcium phosphate, dicalcium phosphate, potassium phosphate monobasic, dipotassium phosphate, tri potassium phosphate, magnesium phosphate, zinc phosphate and sodium phosphate dibasic. In certain liquid inhalation formulations, dicalcium phosphate, is not as soluble as potassium phosphate, which can substitute for it in any inhaled formulation. Calcium can be delivered as calcium chloride, calcium carbonate, calcium acetate, calcium citrate, calcium lactate, and calcium sulfate and calcium pyruvate. Pyruvate can be delivered in many salt forms. Sodium, Potassium, calcium, magnesium and the other salts etc. Magnesium can be delivered as magnesium chloride, magnesium phosphate, magnesium bicarbonate or magnesium sulfate. The PH should be adjusted to 7.4 with sodium hydroxide. Calcium and magnesium are needed for lung enzymes to make phospholipids and phosphate and pyruvate are used as an ingredient in phospholipids. Magnesium is also needed for mitochondrial membrane stability and for the production of ATP. Without the addition of calcium, phosphate or magnesium, pyruvate is converted in the lungs to water, CO2 and acetate. See table III.

Example IV

SaO2 Pilot Study in Subjects with Chronic Hypoxemia and Lung Diseases

A total of five (5) subjects diagnosed with Severe COPD (chronic bronchitis or emphysema) and requiring supplemental oxygen at rest were enrolled in this study at the University of Connecticut. Each subject received a single inhalation dose of either 0.5 mM sodium pyruvate, 5.0 mM sodium pyruvate or 0.9% sodium chloride at each Study Visit. The dose was administered in a blinded cross-over manner at 1-week intervals; such that all subjects received each study compound. Safety and therapeutic efficacy were evaluated by the following measurements: spirometry, expired breath NO level, SaO2, vital signs, and follow-up telephone interviews.

The study was conducted in four visits: a Screening Visit and Study Visits 1-3. The effect of the inhalation of a single dose of sodium pyruvate (0.5 mM and 5.0 mM) or placebo (0.9% sodium chloride) was studied in a double blind protocol. The primary efficacy outcome objective was the SaO2 levels for all subjects. In addition COPD subjects were evaluated by lung function ($FEV_1$ and PEF) and expired breath NO levels obtained just prior to and then at 60 minutes and at 3 hours in the second study, following the administration of the particular sodium pyruvate dose. Since safety has been demonstrated in previous studies, only vital signs were monitored prior to, and post inhalation of, sodium pyruvate.

Pulse oximetry is a simple, cheap, and noninvasive procedure used to measure the level of oxygen (or oxygen saturation) in the blood. Oxygen saturation should always be above 95 percent. However, oxygen saturation may be lower if you have a respiratory disease or congenital heart disease. You can measure the blood's percentage of oxygen saturation using a pulse oximeter, a clip-like sensor device that is placed on your finger. A pulse oximeter may also be used to assess, whether lung medications are working effectively, and to determine patient tolerance to increased activity levels, or patients that suffer from sleep apnea or have a serious medical condition, such as heart attack, congestive heart failure, chronic obstructive pulmonary disease (COPD), anemia, lung cancer, asthma, or pneumonia. Oximeters use the light absorptive characteristics of hemoglobin and the pulsating nature of blood flow in the arteries to measure the level of oxygen in the body. Your oxygen saturation level and pulse rate are displayed in seconds on a lighted display screen. A range of 95% to 100% is generally considered normal. If your oxygen level drops below 85%, you should seek medical attention.

There were no Adverse Events noted in any of the subjects studied. No physiological alterations occurred that caused study termination of any of the participants after the inhalation of sodium pyruvate. No significant change in the $FEV_1$ or SaO2 was observed in any of the subjects after the inhalation of the 0.5 mM or 5.0 mM sodium pyruvate in saline or physiological saline as compared to the pre inhalation values. Nitric oxide levels were increased by 19% with the 5 mM inhaled solution. This explains why sodium pyruvate by itself, without the correct ratio of calcium, phosphate and magnesium did not increase SaO2 levels in patients with severe COPD that have hypoxemia.

Example V

A repeat of this study with 6 patients with various lung and sinus diseases including moderate COPD patients, interstitial lung disease and hypoxemia, showed an increase in FEV-1, SaO2 and no increase level of NO in the patients treated with both the 0.5 mM or 5.0 mM surfactant enhancer (sodium pyruvate formula with calcium, phosphate and magnesium). This formula was rated higher than the standard sodium pyruvate solution without calcium, phosphate and magnesium. See Tables I-III. Both the nasal spray and the nebulized lung solution with the surfactant enhancer (sodium pyruvate formula with calcium, phosphate and magnesium) increased SaO2 in patients with COPD Cystic Fibrosis, Asthma, Allergic Rhinitis, Alzheimer's, interstitial lung disease, cancer and in other lung and sinus diseases by an average of 4%. The inhalation of 20 mM of the surfactant enhancer increased SaO2 by 6% and decreased coughing and lung tightness by 40% over the standard sodium pyruvate formula without calcium, phosphate and magnesium. See table IV In reviewing the literature, it was found that various salts of chloride have been used as carriers of various inhalation drugs for the nasal cavity or lungs, because they have provided no clinical effects or efficacy for the treatment of lung diseases. Sodium chloride is mainly used as nasal or lung moisturizer. All the other salts, calcium chloride, potassium chloride, and magnesium chloride, potassium phosphate, calcium phosphate, have also been used as carrier vehicles and moisturizers. They produce no change to FEV-1 or SaO2 measurements.

It must be noted that there is a difference between people who have transient hypoxemia and those that has permanent hypoxemia. The patients respond differently to the inhalation of sodium pyruvate by itself without calcium, phosphate and magnesium. Sodium pyruvate formulations both given orally or by inhalation will increase SaO2 levels in people without lung injury to the alveoli structure especially the mitochondria that can synthesis the phospholipids needed for oxygen exchange and uptake. Transient hypoxemia is a self correcting effect. It occurs in over exercising, mountain climbing etc. In controlled inhalation studies, patients with no lung injuries or disease, showed an increase of SaO2 by an average of 3% after exercising. Patients with lung damage, like in smokers, which have a 50% rate of hypoxemia, did not show an increase SaO2 levels after inhaling sodium pyruvate without calcium, phosphate and magnesium. See tables I-IV. In patients with infections, i.e. CF and allergic Rhinitis, Nitric Oxide increase by over 400% over base line measurements with the use of the sodium pyruvate, calcium, phosphate and magnesium formula, needed to fight infections and lung cancer (see table IV).

average of 4%. The inhalation of the nasal spray 20 mM sodium pyruvate with calcium, phosphate and magnesium was administered first to all patients followed by the inhalation by nebulization of 5 ml's of the 5 mM sodium pyruvate with calcium, phosphate and magnesium, which increased SaO2 by 6% and decreased coughing and lung tightness by 40% over the standard sodium pyruvate formula without calcium, phosphate and magnesium For the first time a way to increase SaO2 levels in Alzheimer's patients that sodium pyruvate could not do without the addition of calcium, phosphate and magnesium. The ability to enhance the synthesis of brain or lung phospholipids had a dramatic effect on Alzheimer's patient's cognitive ability increasing the score to 70%. Aside from Alzheimer's disease, Parkinson's disease is the most well-known disease in the neurodegenerative disease group. Parkinson's disease (PD) is a chronic and progressive degenerative disease of the brain that impairs motor control, speech, and other functions. Two patients suffering from Parkinson were given inhaled lithium pyruvate (5 ml's of the 1 mM solution with the calcium, phosphate, magnesium formula) everyday for five weeks and in week one of treatment the shaking was substantially reduced in both patients. Pyruvate is one of major energy carriers in the brain, it was shown to be protective against damaging consequences of neurotoxins, such as hydrogen peroxide, glutamate, zinc, and copper/cysteine. Supplementation of

TABLE IV

Percentage measurements in patients with permanent hypoxemia against control group without Hypoxemia. 20 mM sodium pyruvate formula with calcium, phosphate and magnesium were inhaled. Overall rating was 1-10 with 1 being the most negative and 10 being the best result

| Various Lung and sinus diseases | Percentage Increase in FEV-1 | Percentage increase in Nitric oxide over baseline | Percentage Relief of congestion and lung tightness | Percentage decrease in coughing in 4 hours | Percentage Increase in SaO2 over baseline | Lung tightness Overall Rating 1-10 |
|---|---|---|---|---|---|---|
| Control group 5 Moderate COPD without Hypoxemia | 4.0 | 10.0 | 15.0 | 12.0 | 0.5 | 8 |
| Patients with Hypoxemia | | | | | | |
| 15 moderate COPD | 14.0 | 20.0 | 28.0 | 48.0 | 3.0 | 7 |
| 5 Asthmatics | 8.0 | 14.0 | 25.0 | 10.0 | 4.0 | 7 |
| 13 CF | 6.0 | 453.0 | 42.0 | 30.0 | 4.0 | 10 |
| 10 Allergic Rhinitis and various sinus diseases | 12.0 | 43.0 | 68.0 | 22.0 | 5.0 | 10 |
| 5 Alzheimer's patients | 12.0 | 41.0 | 38.0 | 14.0 | 4.5 | 9 |
| 4 Interstitial lung disease | 14.0 | 10.0 | 19.0 | 33.0 | 3.0 | 9 |
| Three patients with lung cancer | 11 | 422 | 15 | 25 | 4 | 10 |

Both the nasal spray and the nebulized lung solution with the sodium pyruvate formula with calcium, phosphate and magnesium, increased Sa02 in patients with COPD Cystic Fibrosis Asthma, Allergic Rhinitis, Alzheimer's, interstitial lung disease and in other lung and sinus diseases by an glucose containing culture media with energy substrates, plus pyruvate, protected rat primary neurons from degeneration and death caused by A-beta peptides characteristic for Alzheimer's disease. Magnesium pyruvate also worked in these patients.

Example VI

Patients with Severe Lung Injury or Mitochondrial Damage or COPD and Hypoxemia with Reduced Lung Capacity Total lung capacity is the volume in the lungs at maximal inflation, the sum of VC and RV.

RV is the residual volume of air remaining in the lungs after a maximal exhalation.

VC vital capacity is the volume of air breath out after the deepest inhalation. Vital capacity in males is 4.8 liters and in women 3.8 liters. Slow vital capacity (SVC) is the maximum volume of air that can be exhaled slowly after slow maximum inhalation.

Three male patients suffering from severe lung injury or mitochondrial damage or COPD and Hypoxemia were treated as described below for two (2) months. Prior to treatment the subjects had limited capacity to breathe, did not respond to any other treatment, were on oxygen daily, and could not function After two (2) months treatment they showed marked improvement. In fact, dramatic results were observed within two (2) weeks. These same three patients were treated in the same way four months earlier using just the sodium pyruvate formulas without the calcium, phosphate and magnesium and showed no or little improvement in lung functions, especially in total lung capacity. One of the three patients with COPD did show an improvement in SaO2 levels at the end of the two months by 3%, but total lung capacity did not change. The second treatment was conducted as follows:

Five (5) milliliters of five (5) millimolar sodium pyruvate with the calcium, phosphate, magnesium solution was filter sterilized through a 0.2 micron filter. The sterile pyruvate solution is placed into a "Pulmo Aid" nebulizer manufactured by DeVilbiss Co., Somerset, Pa. 15501-0635. The sterile pyruvate solution is nebulized by the Pulmo Aid device fitted with a disposable nebulizer and inhaled by the patient. The patient inhales normally from the Pulmo Aid nebulizer until all of the solution has been nebulized and inhaled. This inhalation step typically takes about ten (10) to twenty (20) minutes.

The patients were treated with this inhalation therapy periodically. Initially, treatments are about four (4) times a day at about six (6) hour intervals. Treatments were reduced to three (3) times a day at about eight (8) hour intervals after 20 days of therapy. Treatments were further reduced to once a day 60 DAYS AFTER ONSET OF TREATMENT. After sixty (60) days treatments are three to five times a week.

The following data shows results of various lung capacity and lung function tests administered before treatment and two (2) months after treatment was commenced. Total vital capacity averaged in the three patients increased from 2.2 liters to 3.5 liters, an increase of 33% and $SaO2_2$ levels increased by over 6% in all the patients.

Conclusion: Treatment did the following: (1) Improved lung vital capacity by 33% (2) decreased some medication levels and ceased the use of oxygen. (3) COPD is reduced to the point that routine use of inhalers is not needed. (4) Increased lung capacity by 34%.

Example VII

Clinical Trial 1: Eighteen subjects with allergic rhinitis and various other sinus diseases, who were regular nasal spray users were given EmphyClear™, a Sodium Pyruvate+Saline Nasal Spray to use at home two or three times a day for seven days, in place of their regular nasal spray. Several of these subjects regularly used saline, or OTC nasal products and several used steroid-based nasal sprays. Forty percent of subjects suffered from at least one oropharyngeal disorder; the most frequently reported were hoarseness, tingling, mouth irritation, and reddening do to the use of inhaled steroids.

Prior to, and at the end of the study period, the subjects' nostrils were examined for mucosal fragility, lesions, erythema, and edema using a rhinoscope. These pre- and post-study nasal characteristics were rated on a five point zero ("none") to four ("severe") scale, and compared.

Conclusions

All 18 subjects completed the study, and none opted to return to their normal nasal spray therapy during this period. The data obtained from the rhinoscopic examinations indicated that the Sodium Pyruvate+Saline Nasal Spray did not induce dermal irritation and was effective in significantly (p=0.006) reducing the erythema in subjects who normally use either saline or non-saline nasal sprays including steroids when pre-test ratings were compared to post-test ratings.

Further, subjective evaluations from the subjects indicated a positive preference for the Sodium Pyruvate+Saline Nasal Spray, with 83% of all subjects saying EmphyClear™ was "Better Than" or "Comparable To" their present therapy with regard to "Soothing;" and a like percentage of all subjects saying EmphyClear™ was "Better Than" their present therapy for relieving symptoms.

94% of all subjects said it was "Better Than" their present therapy with regard to less "Stinging." When questioned by the Investigator, 17 of 18 subjects stated that EmphyClear™ "Opened Nasal Passages," and "Cleared Congestion, reduced snoring, and moisturized their nasal passages." These results were consistent whether the subject normally used a saline or steroid-based nasal spray. This study clearly showed that delivery of sodium pyruvate can reduce nasal congestion, swelling, inflammation and enhanced their sleeping. When several of these patients assessed the pyruvate formula with the calcium, phosphate and magnesium against the standard sodium pyruvate solution in saline, they reported the added benefits of, less lung tightness, less mucus production which is do to an increase of sinus and lung surfactants and a reduction of one or more oropharyngeal disorders; hoarseness, tingling, mouth irritation, and reddening.

Example VIII

Fourteen-Day in-Use Evaluation of Nasal Sprays Containing Sodium Pyruvate and Reduced Steroids Nasal Sprays are used by consumers to relieve congestion, nasal dryness, inflammation, itchiness, redness, and other allergy type symptoms. For mild symptoms, nasal sprays containing only saline are typically used by people who suffer from nasal congestion symptoms. However, individuals who have moderate to severe chronic sinus problems with associated nasal inflammation, use nasal sprays that contain steroids. These steroid-containing sprays reduce inflammation and provide superior relief compared to saline-only products. However, chronic use of these steroids can cause problems in the respiratory tract and ultimately lead to "rebound congestion" (Rhinitis Medicamentos). This "rebound congestion" actually worsens the subject's nasal morphology and physiology, leading to increased nasal congestion and inflammation. As a result, the chronic use of steroid nasal sprays is discouraged by the products' manufacturers' and most physicians. Excess use of steroids has also been associated with hypoxemia.

Nine regular Flonase® subjects and eight regular Nasacort® subjects who suffered chronically from nasal decongestion were recruited to evaluate comparable products containing a reduced level of steroids (50-70% reduction in the drug) in a 5 mM sodium pyruvate solution. Prior to beginning the study, the subjects were asked to rate their current product on a 10 point visual analogue scale (VAS) with 0 being "terrible" and 10 being "excellent" for the following categories: soothing the nostrils, relieving symptoms, sting of nostrils, and overall rating of satisfaction. The subjects on average rated their current products "good," with little difference between the two products except for a trend toward perceived better "soothing" with Nasacort® than with Flonase®.

Upon beginning the trial the subjects were blinded regarding their Test Product, and they used the Test Product exclusively for 14 days. The subjects' nostrils were objectively evaluated using a nasoscope at days 0, 7, and 14, and physical exams, including vital signs were also administered on days 0, 7, and 14. During the 14 day test period the subjects subjectively evaluated the Test Product on a daily basis using a 10-point VAS questionnaire. The categories included comparison of the Test Products to the subjects' normal therapy in their ability to sooth the nostrils, relieve symptoms, cause/reduce stinging, relieve decongestion, and quantify usage, and rate the product on an "overall" basis.

After seven and fourteen days, nasoscope evaluations revealed a trend in reduction of aberrant morphologies for the "Reduced-Strength Flonase®" Test Product compared to the nasoscope evaluations obtained on Day 0; and a significant reduction in aberrant morphologies for the "Reduced-Strength Nasacort®" Test Product. These objective observations are consistent with the subjective evaluations where the subjects rated "Reduced-Strength Flonase®" Test Product as "Comparable" or "Better" in all categories, and rated "Reduced-Strength Nasacort®" Test Product as "Better" in all categories.

The Test Products were subjectively judged to be comparable or better than the Flonase® or Nasacort® that the subjects typically used. The subjects did not rate the Test Products lower than the Flonase® or Nasacort® in any category. The Test Products were rated as "Better" in comparison to the "Soothing," "Stinging" and "Relief of Symptoms" characteristics of Flonase®, and, with regard to Nasacort®, the subjects rated the Test Product as "Comparable" across all categories after 14 days of use. End-of-Trial subjective comments were also highly favorable to the Test Products compared to Flonase® and Nasacort®. Additionally, when asked if they might purchase the product, the subjects' average result was 5.4±1.0, indicating that the subjects "Might Purchase," or were "Likely to Purchase," the Test Product. Conclusion: "Reduced-Strength Flonase®" and "Reduced-Strength Nasacort®" Test Product nasal sprays were found to be as effective as the "full-strength" (i.e. commercial) Flonase® and more effective than the commercial Nasacort® when the reduced commercial "active ingredients" were delivered to the subjects in a 5 mM (0.55 mg/mL) sodium pyruvate saline solution. Pyruvate and steroids acted synergistically. By themselves, steroids can be toxic and irritating and habit forming. When placed together with pyruvate, they acted synergistically to reduce inhaled steroid levels and complemented their reactions in the human body. The 5 mM pyruvate solution in combination with reduced steroids, balanced the negative effect of steroids and enhanced the effect of steroids allowing the reduction of steroids by 70% and to obtain the same effect as the full dose of steroids. The sodium pyruvate formula with calcium, phosphate and magnesium, worked better and was less irritating to the nasal cavities and sinuses and produced a reduction in oropharyngeal disorders; including hoarseness, tingling, mouth irritation, and reddening, when compared to the sodium pyruvate in saline alone. Active ingredients in Flonase is fluticasone propionate, in Nasacort is triamcinolone acetonide, in Nasonex is mometasone, in Rhinocort is budesonide.

In a similar experiment described above, a commercial Rhinocort nasal formula (32 mg of budesonide) was diluted with 5 mM sodium pyruvate formulation to deliver 16 mg of budesonide (50% of the commercial formulation) to the 4 patients that use Rhinocort and that suffered with allergic rhinitis and sinusitis, and other nasal inflammatory diseases. These patients rated budesonide 4 on a 1-10 irritation scale with 1 being the most irritating and 10 being non irritating to the sinuses. These patient were squirting each nostril 2-3 times each, two to three times daily, which is 12-18 daily squirts, far exceeding FDA standards of 240 mg daily usage of this steroid. When these patients tested the 50% formulation with sodium pyruvate they obtained the same efficacy, but with half the usage of the steroid, but still using 12-18 squirts daily. They rated the product a 5. When the budesonide was diluted with calcium pyruvate, the patients rated this formula a 6 and reported that they used equal or more squirts to obtain efficacy. When these patients tested the 50% formula with the sodium pyruvate, calcium, phosphate and magnesium formula, they rated the product a 8 and all the patients recorded a 20%-30% reduction in usage, 8-12 squirts daily usage, clearly showing that the sodium pyruvate with calcium, phosphate and magnesium was synergistic and un expectantly less irritating to the nasal cavities and sinuses and reduction of one or more oropharyngeal disorder; hoarseness, tingling, mouth irritation, and reddening. See table V

TABLE V

Comparison of various salts of pyruvate in 5 mM salt solutions with commercial steroids that were diluted by 50% in patients with Allergic Rhinitis at 14 days. Overall rating was 1-10 with 1 being the most negative and 10 being the best result

| Various Salts of pyruvate | Soothing of Nostrils | Relief of symptoms | Stinging of Nostrils | Relief of congestion | Comparison of amount used | Overall Rating 1-10 |
| --- | --- | --- | --- | --- | --- | --- |
| Sodium | | | | | | |
| Nasacort | 6.1 | 5.0 | 6.8 | 6.5 | 6.6 | 6.8 |
| Flonase | 6.0 | 6.1 | 6.2 | 6.8 | 5.9 | 7 |
| Rhinocort | 5.8 | 5.8 | 6.0 | 5.7 | 5.4 | 5.6 |

TABLE V-continued

Comparison of various salts of pyruvate in 5 mM salt solutions with commercial steroids that were diluted by 50% in patients with Allergic Rhinitis at 14 days. Overall rating was 1-10 with 1 being the most negative and 10 being the best result

| Various Salts of pyruvate | Soothing of Nostrils | Relief of symptoms | Stinging of Nostrils | Relief of congestion | Comparison of amount used | Overall Rating 1-10 |
|---|---|---|---|---|---|---|
| Calcium | | | | | | |
| Nasacort | 6.1 | 5.0 | 5.0 | 6.0 | 5.1 | 5.8 |
| Flonase | 5.0 | 5.1 | 5.7 | 5.8 | 5.9 | 6 |
| Rhinocort | 4.6 | 5.0 | 4.8 | 5.1 | 5.1 | 5.5 |
| Sodium pyruvate & calcium & phosphate & magnesium | | | | | | |
| Nasacort | 7.0 | 8.1 | 7.9 | 8.6 | 8.9 | 9 |
| Flonase | 7.8 | 8.5 | 8.6 | 8.5 | 8.8 | 8.9 |
| Rhinocort | 6.8 | 7.4 | 7.8 | 7.5 | 8.3 | 8.4 |

TABLE VI

Comparison of 20 mM sodium pyruvate saline nasal spray to the 20 mM sodium pyruvate formula with calcium, phosphate and magnesium in COPD patients with Allergic Rhinitis tested over a three months period. Overall rating was 1-10 with 1 being the most negative and 10 being the best result

| Formulas | Rating 1-10 decrease in shortness of breath | Percentage decrease in COPD symptoms | Rating 1-10 Congestion and lung tightness | Relief of coughing. Percentage Daily decrease | Percentage decrease in us of RX medications | Overall Rating 1-10 |
|---|---|---|---|---|---|---|
| Sodium Pyruvate in physiological saline | 6.0 | 18.0% | 5 | 15% | 20% | 7 |
| Sodium Pyruvate & calcium & Phosphate & magnesium physiological Saline | 8.0 | 52.0% | 9 | 46% | 48% | 9 |
| | 2.0 | 6% | 4 | 5% | 1.0% | 4 |

Example IX

Evaluation of the Sodium Pyruvate Formula with Calcium, Phosphate and Magnesium to the Sodium Pyruvate Solution without Calcium, Phosphate and Magnesium with Various Drugs in Patients with Injured Lung Mitochondria that have Hypoxemia With the hundreds of patients tested in these various clinical trials, data was gathered as to the type of medications the patients used and the frequency of their use over a six month period. The patients were asked to rate their medications form 1-10 with 1 being the most irritating with the most side effects and 10 being the best with no irritation and no side effects. In these clinical trials, various drugs were evaluated for irritation, mucus production, and efficacy in humans. The drugs were all evaluated using their current formulations and concentrations against the same formulations with the addition of sodium pyruvate, with the calcium, phosphate and magnesium formula given just prior to the use of their medications. They were instructed to inhale this formula just prior to the use of their medications and to evaluate the effect of their medications on the 1-10 scale. Scores are based on user scoring of the product and are on a 1-10 scale with a 1 score being very irritating and having side effects, 5 being comparable to the current product and above 5 being better than the current commercial product (less irritating and fewer side effects) see table VII.

The following medication were evaluated and the ones that worked with the sodium pyruvate, calcium, phosphate and magnesium formula were the nasal and lung steroids Flonase, Nasacort, Nasonex, Tobramycin an antibacterial, Aztreonam lysine an antimicrobial, Zanamivir for the treatment of influenza A and B, Pentamidine isethionate an antimicrobial, Bactroban (Mupirocin) and antibacterial, Ribavirin (an antiviral), Vancomycin for the treatment of Staph infections, Sprix (ketorolac Tromethamine), Patanase for nasal allergies (olopatadine HCl), nicotine, Epinephrine, Cromoglycate, Combivent, acetylcysteine and insulin. All of the medications listed above have three or more of the side effects listed: Chest pain, nausea, vomiting, coughing, bronchospasm, headaches, hypoventilation, hypotension, bradycardia, increased infections, blurred vision, mucosal irritation, fatigue, and shortness of breath and a decrease in SaO2 values. In patients (36) with constant lung infections, bacterial or viral, the 20 mM sodium pyruvate formula with calcium, phosphate and magnesium reduced the amount lung or sinus infections by 54% over the course of a year, which is very significant.

Patients on the various inhaled medications weather inhaled or taken orally or by IV infusion, were enlisted in the evaluation of the inhaled sodium pyruvate phosphate and magnesium formula. The patients were tested for their SaO2 levels and those that had SaO2 levels below 92% were asked to enlist in the study. Nearly 50% of all patients on inhaled medications or other non inhaled medications exhibited Hypoxemia do to their medical conditions or the medications they received. After the SaO2 levels were determined prior to and one hour after taking their medications, the patients returned the following day. SaO2 measurements were taken one hour prior to taking their medications. The patients were then handed the inhalation formula of sodium pyruvate with calcium, phosphate magnesium formula (5 ml's of the 5 mM formula) and instructed to inhale it one hour before taking their medications. SaO2 measurements were then taken one hour after taking their medications. See table VII.

ment with the inhalation of the sodium pyruvate, calcium, phosphate and magnesium increased SaO2 levels by 3% a clinically significant improvement. Only the patients treated with the sodium pyruvate, calcium, phosphate and magnesium formula stated they could breathe better with less lung tightness.

Example X

Mucolytic

The sodium Pyruvate, calcium, phosphate and magnesium solution was assessed with inhaled acetylcysteine which is FDA approved. Inhaled acetylcysteine is indicated for mucolytic ("mucus-dissolving") therapy as an adjuvant in respiratory conditions with excessive and/or thick mucus production. Such conditions include emphysema, bronchitis, tuberculosis, bronchiectasis, amyloidosis, pneumonia, cystic fibrosis and (COPD) Chronic Obstructive Pulmonary Disease. It is also used post-operatively, as a diagnostic aid, and in tracheotomy care. It may be considered ineffective in cystic fibrosis. However, a recent paper in the Proceedings of the National Academy of Sciences reports that high-dose oral N-acetylcysteine modulates inflammation in cystic

TABLE VII

Comparison of various drugs administered in patients with chronic Hypoxemia. Overall rating was 1-10 with 1 being non-effective and 10 being the best result for total lung function tests. Lung functions were measured as reduction in lung tightness and coughing, ease of breathing and decrease in hypoxemia as measured by an increase in SaO2 levels

| Various Drugs | Drugs commercial formula given as instructed in the package Lung functions | Drugs in commercial formula with pre-inhaled sodium pyruvate in saline only Lung functions | Drugs in commercial formula Pre-inhaled sodium pyruvate & calcium & phosphate & magnesium Lung functions | Drug in commercial formula taken in prescribed way. SaO2 measurements taken after medication and compared to baseline SaO2 Measurements | Drug in commercial formula with pre-inhaled sodium pyruvate saline only. measurements taken after taking the medication and compared to baseline SaO2 Measurements | Drug in commercial formula with Pre-inhaled sodium pyruvate, calcium & phosphate & magnesium. measurements taken after taking medication and compared to baseline SaO2 measurements |
|---|---|---|---|---|---|---|
| Pentamidine isethionate | 4 | 5 | 8 | −1 | +1 | +2 |
| Mupirocin | 4 | 6 | 8 | 0 | 0 | +4 |
| Tobramycin | 5 | 5 | 6 | −2 | 0 | +3 |
| Vancomycin | 6 | 5 | 8 | −1 | 0 | +1 |
| Aztreonam | 8 | 8 | 7 | −1 | 0 | +4 |
| Zanamivir | 4 | 5 | 7 | −2 | 0 | +5 |
| Ribavirin | 5 | 6 | 7 | −3 | 0 | +2 |
| Albuterol | 8 | 8 | 8 | 0 | +1 | +4 |
| Patanase | 7 | 7 | 8 | 0 | 0 | 0 |
| Chlotrimizole | 4 | 6 | 8 | −2 | +1 | +1 |
| Epinephrine | 3 | 4 | 5 | +1 | 0 | +6 |
| Cromoglycate | 3 | 6 | 7 | 0 | 0 | +5 |
| Flunisolide | 6 | 6 | 6 | −1 | +1 | +4 |
| Nicotine | 3 | 6 | 8 | −3 | +2 | +4 |
| Insulin | 5 | 6 | 7 | −2 | +1 | +4 |
| Butorphanol | 6 | 7 | 9 | −2 | 0 | 0 |
| Imetrex | 7 | 7 | 7 | −3 | 0 | 0 |
| Acetylcysteine | 4 | 6 | 8 | +1 | 0 | +4 |
| Flonase | 4 | 5 | 9 | 0 | +1 | +5 |
| Levorphanol Tartrate | 2 | 6 | 8 | −6 | +1 | +6 |

As can be seen in table VII the best formula was the sodium pyruvate formula with calcium phosphate and magnesium. The commercial drug formulas listed above by themselves averaged a 5.1. The addition of sodium pyruvate raised that to 6.1, an increase of 17%. The addition of the sodium pyruvate with calcium, phosphate and magnesium raised that to an average of 7.3, a 31% reduction of side effects. The commercial drug formulas listed above by themselves averaged a zero for SaO2 whereas the pretreatfibrosis and has the potential to counter the intertwined redox and inflammatory imbalances in CF. Oral acetylcysteine may also be used as a mucolytic in less serious cases. Inhaled acetylcysteine is indicated for mucolytic ("mucus-dissolving") therapy as an adjuvant in respiratory conditions with excessive and/or thick mucus production. For this indication, acetylcysteine acts to reduce mucus viscosity by splitting disulfide bonds linking proteins present in the mucus (mucoproteins). The sodium Pyruvate, with the calcium, phosphate and magnesium formula was added to a commercial formula of acetylcysteine and was found to enhance its mucolytic activity. When many of these patients assessed the sodium Pyruvate, calcium, phosphate and magnesium formula against the standard sodium pyruvate solution in saline, they reported an added benefit, less lung tightness, less mucus production which is do to an increase of sinus and lung surfactants. The use of pyruvyl-cysteine was as effective as N-acetylcysteine.

Example XI

Horse Racing

When horses race, they sometimes bleed through the nostrils and suffer from hypoxemia. Three horses with breathing and bleeding problems were treated with a 20 mM nasal solution of sodium pyruvate with calcium, phosphate and magnesium (surfactant enhancer). The horses were treated by squirting each nostril 10 times each, one hour before racing and again just a few minutes before racing. The use of the Surfactant enhancer eliminated the bleeding and enhanced the horse's performances. They actually started winning races, whereas they would always loose. Their breathing problems disappeared.

Example XII

Treatment of Migraines

The use of the surfactant enhancer pyruvate nasal spray relieved migraines and blurred vision and congestion in all 15 patients tested. The National Headache Foundation estimates that 28 million Americans suffer from migraines. More women than men get migraines and a quarter of all women with migraines suffer four or more attacks a month; 35% experience one to four severe attacks a month, and 40% experience one or less than one severe attack a month. Each migraine can last from four hours to three days. People with migraines may inherit the tendency to be affected by certain migraine triggers, such as fatigue, bright lights, weather changes, and others. There is a migraine "pain center" or generator in the brain. A migraine begins when hyperactive nerve cells send out impulses to the blood vessels, causing them to clamp down or constrict, followed by dilation (expanding) and the release of prostaglandins, serotonin, and other inflammatory substances that cause the pulsation to be painful.

Many migraines seem to be triggered by external factors. Possible triggers include: Emotional stress, Sensitivity to specific chemicals and preservatives in foods, Caffeine, Changing weather conditions, Menstrual periods, Excessive fatigue, Skipping meals, and Changes in normal sleep pattern.

It became obvious from the results of the clinical trials, that the sodium pyruvate with calcium, phosphate and magnesium formula nasal spray relieved migraines and reduced swelling and congestion and the pain associated with migraines.

Example XIII

Sleep Aids

All the patients that used our 20 mM sodium pyruvate with calcium, phosphate and magnesium formula nasal spray stated they slept better. This nasal spray was then modified by adding tryptophan a known sleep agent found in turkey meat. The addition of tryptophan worked synergistically to enhance sleep in patients that used it. Inhalation products for sleeping disorders were combined with the sodium pyruvate with the calcium, phosphate and magnesium formula. They included, migranal (dihydroergotamine mesylate) stadol (butorphanol), lmetrex (sumatriptan succinate), for anti snoring. Two children with Autism, reported that the use of the 20 mM sodium pyruvate with the calcium, phosphate and magnesium formula nasal spray calmed them down and allowed them to sleep all night.

Example XIV

Sleep Apnea

Sleep Apnea is a sleep disorder characterized by pauses in breathing or instances of shallow or infrequent breathing during sleep, with a reduction in SaO2 values caused by reduced levels of synthesized phospholipids. Each pause in breathing, called an apnea, can last for several seconds to several minutes, and may occur, by definition, at least 5 times in an hour. Similarly, each abnormally shallow breathing event is called a hypopnea. When breathing is paused, carbon dioxide builds up in the bloodstream. Chemoreceptors in the blood stream note the high carbon dioxide levels. The brain is signaled to wake the person sleeping and breathe in air. Breathing normally will restore oxygen levels and the person will fall asleep again. There are three forms of sleep apnea: central (CSA), obstructive (OSA), and complex or mixed sleep apnea (i.e., a combination of central and obstructive) constituting 0.4%, 84%, and 15% of cases, respectively. In CSA, breathing is interrupted by a lack of respiratory effort; in OSA, breathing is interrupted by a physical block to airflow despite respiratory effort, and snoring is common. According to the National Institutes of Health, 12 million Americans have OSA. There are more cases of sleep apnea still because people either do not report the condition or do not know they have sleep apnea. In other words, common effects of sleep apnea include daytime fatigue, a slower reaction time, and vision problems. OSA may increase risk for driving accidents and work-related accidents. If OSA is not treated, one has an increased risk of other health problems such as diabetes. Even death could occur from untreated OSA due to lack of oxygen to the body. There is also evidence that the risk of diabetes among those with moderate or severe sleep apnea is higher. There is also increasing evidence that sleep apnea may also lead to liver function impairment, particularly fatty liver diseases.

People who smoke have sleep apnea at three times the rate of people who have never smoked. Mild occasional sleep apnea, such as many people experience during an upper respiratory infection, may not be important, but chronic severe obstructive sleep apnea requires treatment to prevent low blood oxygen (hypoxemia), sleep deprivation, and other complications.

Snoring is a common finding in people with this syndrome. Snoring is the turbulent sound of air moving through the back of the mouth, nose, and throat.

The sodium Pyruvate formula with calcium, phosphate and magnesium increased lung and sinus surfactants to decrease congestion and inflammation and increases oxygen saturation to help patients with Sleep Apnea. In all of the clinical studies, approximately 20% of the patients treated with this nasal spray or inhalation therapy (460 patients), reported that they suffered from Sleep Apnea, and that the use of the inhaled surfactant enhancer formula, allowed them to sleep all night without snoring or waking up.

Example XV

Smokers, How Nicotine Inhalation in the Sinuses or Lungs Increases Hypoxemia

The primary therapeutic use of nicotine is in treating nicotine dependence in order to eliminate smoking with its health risks. Nicotine can also be irritating and has the ability to lower SaO2 values when inhaled in smoke while increasing hypoxemia. Nicotine was placed into the sodium pyruvate and calcium, phosphate and magnesium formula. This formula weather delivered nasally or into the lungs, was well tolerated over nicotine by itself, which was irritating. The combination was synergistic. Smokers who used this formula rated the sodium pyruvate, calcium, phosphate and magnesium nicotine formula much higher than nicotine by itself. They reported that nicotine delivered this way was faster than the patch and much less irritating. The patient squirted each nostril three times which is equivalent to 0.66 mg of pyruvate per dose per nostril which is 1.32 mg of pyruvate being delivered per dose times 2 times per day is 2.64 mg of pyruvate delivered per daily dose. Approximately 0.020 mg to 0.03 mg of nicotine was delivered. Nicotine delivered only with sodium pyruvate in saline solution, was a little more irritating and the ability of each patient to determine the effect of nicotine was delayed by 26%. SaO2 levels in these patients rose by 4% with the sodium pyruvate, calcium, phosphate magnesium formula.

Example XVI

Cancer Drugs Often Cause Lung Cell Damage and Inhibit the Synthesis of Membrane Phospholipids to Cause Lung Tightness, Coughing and Hypoxemia The use of a surfactant enhancer might offer promise in battling lung cancer, the leading cause of cancer-related deaths in the United States, and the second-most common cancer overall, according to the National Cancer Institute (NCI). About 160,000 Americans died from the disease last year, which costs the U.S. nearly $10 billion in medical bills, according to the NCI.

Some chemotherapy drugs can affect the lungs (pulmonary toxicity). The exact effect of chemotherapy drugs that cause lung problems is not fully known. It may be that the drugs cause damage in the lung cells that result in a lung infection (pneumonitis). The drugs may also cause fibrous, scar-like tissue to form in the lungs (pulmonary fibrosis) and restrict lung function. Lung damage is often related to the dose of the drugs used. Chemotherapy drugs that are known to cause lung damage are: Bleomycin (Blenoxane)—most common. Lung damage occurs in up to 10% of people who receive this drug. The risk increases when higher doses are used. With Carmustine (BiCNU, BCNU) lung damage occurs in about 20%-30% of people who receive high-dose therapy with this drug. Methotrexate pulmonary toxicity occurs in up to 8% of people who receive this drug. With Alkylating drugs, such as cyclophosphamide (Cytoxan, Procytox) or busulfan (Busulfex) lung damage occurs in less than 1% of people who receive these drugs. Lung damage occurs more often in people who: are elderly, people over 70 years of age, have a higher risk of developing lung problems, have a personal history of lung disease, like COPD, or have received radiation therapy to the lungs. Symptoms of lung damage include: dry cough, shortness of breath (especially with activity) lung tightness, and fatigue. Symptoms can occur during treatment with chemotherapy or a few months after treatment ends. Damage to the lung tissue is usually not reversible.

Changes to lung tissue may be detected with: blood tests to check the level of oxygen in the blood, such as blood gas analysis or oxygen saturation tests that measure lung function, such as pulmonary function test (PFT). When shortness of breath occurs, it may be treated with: oxygen therapy and drugs to reduce inflammation, bronchodilator drugs to widen the bronchi (large tubes, or airways, in the lungs).

Hypoxia within regions of solid tumors including lung cancers, is associated with resistance to standard treatments, particularly radiotherapy. Conventional drug therapy, which depends on reaching the cancer through the bloodstream, can be less effective in hypoxic tumors. Low oxygen levels in a cell interrupt the activity of oxidative phosphorylation, a term for the highly efficient way that cells normally use to convert food to energy. As oxygen decreases, the cells switch to glycolysis to produce their energy units, called ATP. Glycolysis is a drastically less efficient way to obtain energy, and so the cancer cells must work even harder to obtain even more food, specifically glucose, to survive. When oxygen levels dip dangerously low, angiogenesis, or the process of creating new blood vessels, begins. The new blood vessels provide fresh oxygen, thus improving oxygen levels in the cell and tumor and slowing the cancer growth—but only temporarily.

Drug designers have taken advantage of the hypoxic regions in tumors and designed anticancer drugs that are specifically active or activated under hypoxic conditions. For example, hypoxia-activated prodrugs like 3-bromopyruvate, are chemically modified to be inactive, but when administered to the body and exposed to hypoxic conditions (such as in a tumor), they are metabolized or otherwise converted into the active, anticancer form. Despite these new drugs, there is an ongoing need for innovative approaches to anticancer therapy. This patent highlights various treatment options available for increasing lung surfactants that are responsible for increasing blood oxygen levels in cancer Patients thus targeting hypoxic cells within tumors that could be highly beneficial in the treatment of SCLC.

Example XVII

Pretreatment of Normal Cells Co Cultured with Cancer Cells, Followed by Treatment with Doxorubicin Peripheral blood monocytes and U937 monocytic leukemia tumor cells were placed in sterile culture flasks and maintained in culture using Dulbecco's Minimal Essential Medium, with 10% fetal calf serum, supplemented with 2 mM glutamine and Pen/Strep. The cytotoxicity of the cytotoxic agent on the cells was analyzed by propidium iodide exclusion techniques and flow cytometric quantitation. Viability of the cells was quantified as the number of cells that excluded the vital dye trypan blue. Sodium pyruvate was dissolved in distilled water and the solution was adjusted to pH 7.4 with calcium, phosphate and magnesium Solutions were sterile filtered. Stock solutions were prepared so that the vehicle would not be more than 1% of the total volume of the culture media. H-Thymidine Radiosotopic Incorporation Measurement of Cytotoxity The membrane surfactant enhancers agents (sodium pyruvate and calcium, phosphate and magnesium), was examined for their ability to decrease the cytotoxicity of Doxorubicin to U937 monocytic leukemia cells and normal peripheral blood monocytes. The optimal concentrations of the agents that were able to protect cells against Doxorubicin induced Cytotoxicity were the 5 mM of sodium pyruvate, calcium, phosphate and magnesium formula. Susceptibility studies were conducted to determine the optimal treatment time of the cells with the cryoprotective agents prior to treatment of the cells with the cytotoxic agent. The normal cells and U937 leukemic tumor cells were pretreated separately in "wash out" studies with the single agents alone, and in combination, at the optimal concentration described above for various time periods, washed with fresh medium to remove the agents, and treated with the cytotoxic agent.

The surfactant enhancer combination of 5 mM sodium pyruvate and calcium, phosphate, and magnesium formula, provided significant protection to the normal peripheral monocytes and did not protect the tumor cells from the effects of the Cytotoxic agent.

Wash-out studies were conducted to determine viability of the peripheral blood monocytes co-cultured with U937 monocytic leukemia cells after 24 hour pretreatment of the cells with the surfactant enhancer, which is also a mitochondrial protective agent, followed by administration of Doxorubicin. The viability of the control normal peripheral cells was enhanced from 55% to 68% with the use of 5 mM sodium pyruvate and calcium, phosphate and magnesium formula, whereas the viability of the control U937 cells was decreased from 43% to 12%. Thus the use of the surfactant synthesis enhancer protected normal cells for 24 hours, while the leukemia cells died. See table VIII.

TABLE VIII

Comparison of various cancer drugs in various media.
Percentage of viable non cancerous cells after incubation with anticancer drugs

| Various Drugs | Percentage of viable cells after incubation with drugs | Drugs in commercial formula with sodium chloride only | Drugs in commercial formula withسodium pyruvate without calcium & phosphate & magnesium | Drugs in commercial formula with sodium pyruvate with calcium & phosphate & magnesium | Drugs in commercial formula with sodium pyruvate with calcium & phosphate & Magnesium repeat study |
|---|---|---|---|---|---|
| anastrozole | 24 | 25 | 50 | 86 | 94 |
| Bleomycin | 31 | 33 | 47 | 98 | 98 |
| cisplatin | 46 | 43 | 58 | 88 | 91 |
| Carboplatin | 42 | 50 | 56 | 87 | 97 |
| floxuridine | 38 | 38 | 58 | 92 | 91 |
| methotrexate | 42 | 43 | 68 | 94 | 98 |
| oxaliplatin | 23 | 24 | 41 | 95 | 98 |
| Bevacizumab | 21 | 27 | 40 | 88 | 87 |

The co-culture of normal and U937 leukemic minor cells was treated essentially in the same manner except that the cells were not treated separately, but co-cultured. The optimal pretreatment time of the cells with the membrane enhancer agents was found to be 24 hours prior to treatment of the cells with Doxorubicin. The cells were then placed in culture medium without the protective agents. The length of time that the cytoprotection lasted was 24 hours following Doxorubicin treatment. At this time, peripheral cell viability is a limiting factor because these cells are normal cells and do not remain in culture for extended periods of time.

Normal and U937 tumor cells were co-cultured and the cytotoxity of Doxorubicin on the cells was determined by viability assays which examined the differential ability of the cytoprotective compositions alone, and in combinations, to protect the normal cells from the cytotoxity of the chemotherapeutic agent.

The cells were isolated and examined for morphological evidence of cytotoxicity or prevention of cytotoxicity. These studies determined the cytoprotective effect of the surfactant enhancer on the normal and tumor cells. DNA synthesis studies using 3H-thymidine (1 uCi/well) were carried out 4 hours prior to termination of the experiment to determine the effect of the formulations on the proliferation of the cells as a measure of the prevention of cytotoxicity and the extent of Doxorubicin-induced cytotoxicity. Propidium iodide exclusion analysis was carried out for direct quantitation of the cytotoxicity and the prevention of cytotoxicity. Each set of studies was performed in triplicate so that statistical analysis of the significant differences between the treatment groups could be conducted.

Other drugs tested produced similar results as stated in the above table. They included Crizotinib, Docetaxel, Erlotinib, Etoposide, Gemcitabine, Irinotecan, Paclitaxel, Pemetrexed, Vinorelbine Example XVIII Treatment of Patients with Various Cancers and Lung Cancer To date most patients with cancer that are treated with radiation or cancer drugs show a partial reduction of tumor sizes, but in most cases the cancer remains and life expectances increases for a short period of time. This is the case for lung cancer. Five patients with various cancers including lung cancers were treated with 3-Bromopyruvate, an alkylating agent and a well-known inhibitor of energy metabolism. Results to date have been mixed. The problem with most cancer drugs is not only their toxicity to noncancerous tissue, but is their inability to completely eradicate the cancer. Cancer drugs cause hypoxia in normal noncancerous cells and they destroy lung tissue and their ability to synthesize lung surfactants, thus cause damage to surrounding tissue. In mice studies conducted by others, they investigated the chemo preventive activity of 3-bromopyruvate. For the aerosol treatment the mice were treated with 10-30 mg/5 ml daily and treated for 8 weeks. Aerosolized 3-bromopyruvate significantly decreased tumor multiplicity and tumor load by 40% and 60%, respectively, at a dose of 10 mg/5 mL by inhalation. Interestingly, the efficacy of aerosolized 3-bromopyruvate did not accompany any liver toxicity indicating that it is a safer route of administering this compound. Treatment with 3-bromopyruvate in tissue cultures of lung cancer cells showed an increased immune histo chemical staining for cleaved caspase-3, suggesting that the lung tumor inhibitory effects of 3-bromopyruvate were through induction of apoptosis. 3-Bromopyruvate also dissociated hexokinase II from mitochondria, reduced hexokinase activity, and blocked energy metabolism in cancer cells, finally triggered cancer cell death and induced apoptosis through caspase-3, and PARP in human lung cancer cell line. The problem with 3-bromopyruvate was its toxicity to normal lung cells. The formula needed to protect non-cancerous cells from 3-bromopyruvate and to enhance its effect on tumors, was the addition of inhaled 5 ml's of the 20 mM solution of sodium pyruvate, calcium, phosphate, magnesium formula inhaled 1-2 hours prior to the inhalation of the 10 mg of 3-bromopyruvate. The investigators were given the sodium pyruvate with calcium, phosphate and magnesium formula and instructed to have the mice inhale the formula 1-2 hours prior the inhalation of the cancer drug. This approach reduced tumor sizes by 90% compared the 60% reduction with 3 bromopyruvate by itself. The addition of dichloroacetate with 3-bromopyruvate to the sodium pyruvate with calcium, phosphate and magnesium formula was the best formula decreasing tumor loads by 95%, especially with the addition of magnesium bicarbonate that increased the PH to 7.9 to neutralize the lactic acid produced in tumors that enhance tumorigenesis. Similar effects were seen with the inhalation of the sodium pyruvate, calcium, phosphate, and magnesium formula followed in two hours by oral or inhalation administration of the 3-bromopyruvate or doxorubicin.

Example XIX

Tumor Volume Decrease at 8 Weeks is Associated with Longer Survival in EGFR-Mutant Advanced Non-Small-Cell Lung Cancer Patients Treated with EGFR TKI Departments of *Imaging, †Biostatistics and Computational Biology, Dana-Farber Cancer Institute, Boston, Mass.; †Department of Medical Oncology and Medicine, Dana-Farber Cancer Institute and Brigham and Women's Hospital, Boston Mass.; and Department of Radiology, Brigham and Women's Hospital, Boston Mass.

Background: The study investigated whether tumor volume changes at 8 weeks of therapy is associated with outcomes in advanced non-small-cell lung cancer (NSCLC) patients harboring sensitizing epidermal growth factor receptor (EGFR) mutations treated with EGFR tyrosine kinase inhibitors (TKIs).

Methods: In 56 advanced NSCLC patients with sensitizing EGFR mutations treated with first-line erlotinib or gefitinib, tumor volumes of dominant lung lesions were measured on baseline and follow-up computed tomography, and were analyzed for association with survival.

Results: Among 56 eligible patients, the median tumor volume was 17.8 cm$^3$ (range, 1.3-172.7 cm$^3$) on the baseline scans. Forty-nine patients had follow-up computed tomography at approximately 8 weeks; the median tumor volume at 8 weeks was 7.1 cm$^3$ (range, 0.4-62.3 cm$^3$), with the median proportional volume change of −59% (range, −90% to +91%) from baseline. The proportional volume change at 8 weeks was associated with survival (p=0.02). Using the cutoff value of 38% volume decrease (75th percentile) at 8 weeks, patients with volume decrease more than 38% (n=37) had a median overall survival of 43.5 months compared with 16.3 months among those with volume decrease of 38% or less (n=12; p=0.01). The median progression-free survival for patients with more than 38% volume decrease was 12.6 months, compared with 5.5 months for those with 38% or lesser volume decrease (p=0.2). The 12 patients with 8-week volume decrease of 38% or lesser had significantly shorter survival. The present study demonstrated that proportional tumor volume decrease at 8 weeks of therapy was associated with prolonged survival in advanced NSCLC patients, with sensitizing EGFR mutation treated with first-line gefitinib or erlotinib.

Example XX

Cancer Trial Pilot Study

In eleven patients with various cancers and chronic Hypoxemia, five with lung cancer, including three with non small cell lung cancer and six with various other cancers, were given the formula containing the sodium pyruvate with calcium, phosphate and magnesium by inhalation, which increased SaO2 levels in these patients to enhance the effect of the chemotherapy or radiation, and increased the synthesis of lung surfactants in lung alveoli cells to protect normal cells and help reduce hypoxia in cancer cells. These patients inhaled the formula one to two hours before they were treated with cancer drugs or radiation, given by current standard methods, and continued to inhale the surfactant enhancer formula twice a day for the eight weeks following the chemo therapy treatment. Because these patients are older, they often lack good nutritional eating habits, which effects their immune system.

Thus, the patients were also given a proprietary diet high in a unique blend of antioxidants, and nutrients, that they consumed every day before and after chemo or radiation. Good nutrition is always a plus when patients undergo chemo or radiation as sited in numerous published articles. The diet specifically designed for patients with cancer and hypoxemia included calcium pyruvate, dicalcium phosphate and magnesium in their components. The diet included Lecithin which contains Phosphatidylcholine one table spoon daily needed for phospholipid synthesis in cells and mitochondria and to protect them from chemo, calcium pyruvate 6 grams daily, Magnesium pyruvate 1 gram with 350 mg of magnesium needed by mitochondrial enzymes, calcium phosphate or dicalcium phosphate 1 gram needed by cellular enzymes to maintain hemostasis, Baker's yeast one oz. scoop daily to provide other pre cancer nutrients and vitamin E 400 units or more.

In patients with severe Hypoxemia, Oxygen therapy was continued and the patient also inhaled the surfactant enhancer formula prior to and after chemotherapy for eight weeks. These patients continued chemo therapy beyond the eight weeks and ten patients are still alive six to 10 years later, beating the national survival rate by 4 years.

Other drugs tested given by IV or oral standard treatments reduces tumor sizes or loads by an average 29.2% as sited in the literature. These drugs were Crizotinib, Docetaxel, Erlotinib, Etoposide, Gemcitabine, Irinotecan, Paclitaxel, Pemetrexed, Vinorelbine. The inhalation of the surfactant enhancer decreased tumor loads and sizes, that was averaged among the eleven patients by 54.5%, a statistically and clinically significant result. This clearly showed that decreasing hypoxemia and increasing oxygen levels at hypoxia tumor sites increased the efficacy of chemotherapy or radiation and enhanced the reduction of tumor loads and sizes which increases survival rates significantly. One patient with lung cancer and pulmonary hypertension and COPD was treated with various cancer drugs including Gefitinib, erlotinib or doxorubicin over a year period. His lung cancer did not respond well to any of the treatments and his tumors shrank by only 15%. Pulmonary arterial hypertension causes the arteries that carry blood from the heart to the lungs to narrow, resulting in decreased oxygen flow to the blood vessels. When the body is deprived of vital oxygen, the blood pressure in the pulmonary arteries spikes above the normal range compressing the heart's right ventricle. The pressure on this area will eventually cause the right side of the heart to swell, gradually weaken, and restrict blood flow to the lungs. If left untreated, pulmonary hypertension can end in heart failure. The current treatment is the inhalation of Nitric oxide gas. As stated in table III the addition of the N-acetylcysteine to the phospholipid membrane enhancer formula increased Nitric oxide dramatically over any other pyruvate salt formulas. We had the patent pre and post inhale the sodium pyruvate with calcium, phosphate and magnesium formula with the addition of the N-acetylcysteine during the next round of chemotherapy. His $SaO2_2$ levels rose by 5% and his nitric oxide levels increased by over 225% compared to the standard sodium pyruvate formula in saline, without the addition of calcium, phosphate and magnesium, that raises nitric oxide by 19%, a 11 times greater increase. His tumor load and size shrank by 78% in eight weeks and in his next round of treatment the tumors disappeared. His pulmonary hypertension also disappeared. He is still alive four years later, beating the odds on survival.

Aeroshot Inc sells a caffeine inhaled product that delivers 100 mg of caffeine. One of the patients with lung cancer that was treated with cisplatin used the Aeroshot product along with the surfactant enhancer and decreased tumor sizes by 60% in eight weeks. Caffeine is thought to increase the antitumor effect of cisplatin or DNA-damaging agents because it is known that caffeine inhibits DNA repair. It appears from the results in this patient that the addition of caffeine to the surfactant enhancer (sodium pyruvate with calcium, phosphate and magnesium) enhanced the effect of the cisplatin.

Example XXI

Immunotherapy's Especially for Non-Small Lung Cancer

Keytruda (pembrolizumab), Yervoy (ipilimumab), Opdivo (nivolumab), Tecentriq (atezolizumab) are medicines that may treat your lung cancer by working with your immune system. They can cause your immune system to attack normal organs and tissues in many areas of your body and can affect the way they work. These problems can sometimes become serious or life-threatening and can lead to death. These problems may happen anytime during treatment or even after your treatment has ended. Serious side effects may include lung problems (pneumonitis).

Symptoms of pneumonitis may include: new or worsening cough; chest pain; and shortness of breath. In all these cases these drugs increase hypoxemia by inhibiting the synthesis of lung surfactants. Several patients that reported lung problems with the use of these medications (new or worsening cough; chest pain; and shortness of breath) were given our inhaled formula containing the sodium pyruvate, with calcium, phosphate and magnesium. They reported that their lung problems were eliminated, after using the inhaled formula.

Example XXII

Four-Week Use of Oxymetazoline Nasal Spray Once Daily at Night Induces Rebound Swelling and Nasal Hyperreactivity that can be Reversed with the Addition of the Sodium Pyruvate, Dicalcium Phosphate Magnesium Formula. Ohio State University Medical Center 2001

A randomized double-blind parallel study with 90 healthy volunteers was performed to examine the effect of oxymetazoline nasal spray on the development of rhinitis medicamentosa. For 30 days, 45 subjects were given oxymetazoline nasal spray once daily at night and placebo in the morning and at noon, The other 45 patients were given oxymetazoline nasal spray with 20 mM sodium pyruvate with calcium, phosphate and magnesium by inhalation, which increased SaO2 levels in these patients once daily at night and placebo in the morning and at noon, Before and after the course of treatment, the mucosal surface positions were determined with rhinostereometry, followed by histamine challenge tests. In the morning and the evening just before use of the nasal spray, symptoms of nasal stuffiness were evaluated on visual analogue scales (0-100). After 30 days, rebound swelling and nasal stuffiness occurred only in the oxymetazoline group without the addition of the pyruvate formula. In the group receiving oxymetazoline nasal spray once daily at night, the mean rebound swelling was 1.1 mm (p<0.01) and the estimated mean symptom score for nasal stuffiness in the evening was 43 (p<0.05). In the group receiving oxymetazoline with the pyruvate formula, nasal spray once daily at night, the mean rebound swelling was 0.1 mm (p<0.01) and the estimated mean symptom score for nasal stuffiness in the evening was 3 (p<0.05). The finding of an increase in histamine sensitivity in the oxymetazoline without the pyruvate formula, was taken to indicate nasal hyperreactivity. It is concluded that the risk of developing rebound swelling and nasal hyperreactivity remains, with oxymetazoline nasal spray when used once a day for 30 days, but not when Oxymetazoline contained the sodium pyruvate formula with calcium, phosphate and magnesium.

Example XXIII

Concussions

The secondary effects of cranial trauma that may further compromise brain function are edema, hypoxia, hemorrhage, infection and oxygen radicals. Other important components of posttraumatic cerebral pathophysiology include, but are not limited to, generation of lactic acid, decreased intracellular magnesium, free radical production, inflammatory responses, and altered neurotransmission. Concussions also cause impaired mitochondrial oxidative metabolism that worsens the energy crisis in the brain. Edema may be the result of diffuse shearing of capillary, glial, and neuronal membranes or may be secondary to local contusion or laceration. Edema can generate local pressure that can compromise both arterial and venous cerebral blood flow, causing ischemia and more edema. This may precipitate a vicious cycle sometimes impossible to reverse. The mass effect of edema, focal or diffuse, can cause rostro caudal brain stem deterioration (possibly with herniation), a major cause of delayed death from head trauma. Brain dysfunction and destruction are aggravated by hypoxia, the result of compromised respiratory function caused by the following: (1) injury to the chest, (2) aspiration pneumonia in the unconscious patient, (3) respiratory center depression from rostro caudal deterioration or direct damage to the medulla, (4) pulmonary edema secondary to hypothalamic-septal damage, or (5) status epilepticus. Blood loss from multiple injuries and, as mentioned, brain edema further compromise delivery of oxygen to the brain. We gave several football players the 20 mM sodium pyruvate with calcium, phosphate and magnesium by inhalation, which increased SaO2 levels in these patients, to reduce brain damage and hypoxia. Measurement of reaction times can be measured by the speed of the mouse clicks to common questions. Someone with a concussion will react slowly to these questions. The inhalation of the 20 mM sodium pyruvate with calcium, phosphate and magnesium formula, increased reaction times by 42% over the baseline measurements. In the treatments of patients with concussions or Alzheimer's, the inhalation formulas were delivered by inhalation using a breathing mask.

Smoke Inhalation Damage and Treatment.

The same approach can be applied to smoke inhalation damage. The results indicate that the current pathophysiologic concept is of a disease process that leads to immediate and delayed pulmonary injury. The lung injury process is activated by toxins in the smoke's gas and particle components and by a resulting in lung inflammation. This inflammatory process becomes self-perpetuating through the activation of a large number of inflammatory cytokines and oxygen radicals, which reduce the ability of the lungs to synthesize phospholipids. Several patients with smoke inhalation damage used the mask and testing showed an increase in SaO2 after the inhalation of the sodium pyruvate, calcium, phosphate and magnesium formula and reduced coughing.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

What I claim is:

1. A composition to simulate the synthesis of human lung and sinus surfactants, which treats hypoxemia and dyspnea, consisting of:
   a) saline;
   b) sodium pyruvate;
   c) a phosphate selected from the group consisting of a calcium phosphate, a potassium phosphate, magnesium phosphate, and zinc phosphate and combinations thereof;
   d) a salt of calcium selected from the group consisting of calcium chloride, calcium carbonate, calcium acetate, calcium citrate, calcium lactate, calcium sulfate, and combinations thereof; and,
   e) a salt of magnesium selected from the group consisting of magnesium chloride, magnesium phosphate, magnesium sulfate, magnesium bicarbonate, and combinations thereof.

2. The composition of claim 1, wherein said phosphate is a calcium phosphate selected from the group consisting of calcium phosphate, di-calcium phosphate and combinations thereof.

3. The composition of claim 1, wherein said phosphate is a potassium phosphate selected from the group consisting of potassium phosphate, di-potassium phosphate, tri-potassium phosphate, and combination thereof.

4. The composition of claim 3, wherein said composition is a saline solution consisting of sodium chloride, sodium pyruvate, calcium chloride, potassium phosphate and magnesium chloride.

5. The composition of claim 1, wherein the amount of sodium pyruvate ranges from about 0.0001 mg to about 1 gram, and the amount of each of the phosphate, salt of calcium and salt of magnesium ranges from 0.0001 mg to about 1 gram.

6. The composition of claim 1, wherein said composition is a saline solution consisting of sodium chloride, sodium pyruvate, calcium chloride, potassium phosphate and magnesium chloride.

* * * * *